United States Patent
Chang et al.

(10) Patent No.: US 10,913,068 B2
(45) Date of Patent: Feb. 9, 2021

(54) TESTING DEVICE, MICROFLUIDIC CHIP AND NUCLEIC ACID TESTING METHOD

(71) Applicants: Nanyang Technological University, Singapore (SG); Agency for Science, Technology And Research, Singapore (SG); The Methodist Hospital, Houston, TX (US)

(72) Inventors: Joseph Sylvester Chang, Singapore (SG); Geok Soon Lim, Singapore (SG); Lei Zhang, Singapore (SG); Zhiping Wang, Singapore (SG); Ruige Wu, Singapore (SG); Stephen T. C. Wong, Houston, TX (US); Kemi Cui, Houston, TX (US)

(73) Assignees: Nanyang Technological University, Singapore (SG); Agency For Science, Technology and Research, Singapore (SG); The Methodist Hospital, Houston, TX (US)

( * ) Notice: Subject to any disclaimer, the term of this patent is extended or adjusted under 35 U.S.C. 154(b) by 409 days.

(21) Appl. No.: 15/557,957

(22) PCT Filed: Mar. 14, 2016

(86) PCT No.: PCT/SG2016/050116
§ 371 (c)(1),
(2) Date: Sep. 13, 2017

(87) PCT Pub. No.: WO2016/148646
PCT Pub. Date: Sep. 22, 2016

(65) Prior Publication Data
US 2018/0214878 A1 Aug. 2, 2018

Related U.S. Application Data

(60) Provisional application No. 62/133,014, filed on Mar. 13, 2015.

(51) Int. Cl.
*B01L 7/00* (2006.01)
*C12Q 1/686* (2018.01)
(Continued)

(52) U.S. Cl.
CPC ............... *B01L 7/52* (2013.01); *A61B 5/153* (2013.01); *A61B 5/15003* (2013.01);
(Continued)

(58) Field of Classification Search
CPC ............... C12Q 1/686; C12Q 2600/16; C12Q 2600/158; C12Q 2521/107;
(Continued)

(56) References Cited

U.S. PATENT DOCUMENTS

2005/0059166 A1* 3/2005 Markes ................. G01N 21/03
436/514
2008/0176755 A1 7/2008 Amundson et al.
(Continued)

FOREIGN PATENT DOCUMENTS

WO WO 2015/061299 A2 4/2015

OTHER PUBLICATIONS

*Real-Time PCR*; BIOS Advanced Methods, edited by M. T. Dorak, Taylor & Francis Group (2006) 362 pages.
(Continued)

*Primary Examiner* — Gautam Prakash
(74) *Attorney, Agent, or Firm* — Alston & Bird LLP

(57) ABSTRACT

A testing device is provided. The testing device includes a capturing tool and a microfluidic chip having a plurality of chambers connected in a network, a sample receiving port connected to the network, and a guide structure configured to receive the capturing tool, wherein the capturing tool is configured to capture sample in a distal position from the guide structure and further configured to transfer the cap-
(Continued)

tured sample to the sample receiving port in a proximal position from the guide structure.

9 Claims, 22 Drawing Sheets

Specification includes a Sequence Listing.

(51) Int. Cl.
A61B 5/15 (2006.01)
A61B 5/153 (2006.01)
C12Q 1/6851 (2018.01)

(52) U.S. Cl.
CPC .. *A61B 5/150358* (2013.01); *A61B 5/150389* (2013.01); *A61B 5/150503* (2013.01); *A61B 5/150832* (2013.01); *C12Q 1/686* (2013.01); *C12Q 1/6851* (2013.01); *B01L 2200/10* (2013.01); *B01L 2300/027* (2013.01); *B01L 2300/0681* (2013.01); *B01L 2300/0838* (2013.01); *B01L 2400/0433* (2013.01); *B01L 2400/0481* (2013.01); *B01L 2400/0487* (2013.01); *B01L 2400/0605* (2013.01); *C12Q 2521/107* (2013.01); *C12Q 2563/149* (2013.01); *C12Q 2565/629* (2013.01); *C12Q 2600/112* (2013.01); *C12Q 2600/118* (2013.01); *C12Q 2600/158* (2013.01); *C12Q 2600/16* (2013.01)

(58) Field of Classification Search
CPC ........ C12Q 2600/118; C12Q 2600/112; C12Q 2565/629; C12Q 2563/149; B01L 7/52; B01L 2200/10; B01L 2300/027; B01L 2300/0681; B01L 2300/0838; B01L 2400/0433; B01L 2400/0481; B01L 400/0487; B01L 2400/0605; A61B 5/15003; A61B 5/150358; A61B 5/150389; A61B 5/150503; A61B 5/153; A61B 5/150832
See application file for complete search history.

(56) References Cited

U.S. PATENT DOCUMENTS

| | | |
|---|---|---|
| 2010/0159582 A1 | 6/2010 | Ismail et al. |
| 2010/0297640 A1 | 11/2010 | Kumar et al. |
| 2011/0207140 A1 | 8/2011 | Handique et al. |
| 2011/0269121 A1 | 11/2011 | Gaitas et al. |
| 2014/0038193 A1 | 2/2014 | Spoto et al. |

OTHER PUBLICATIONS

*Real-Time PCR; Understanding $C_T$,* Applied Biosystems, (2008) 6 pages.
International Search Report and Written Opinion for Application No. PCT/SG2016/050116 dated May 3, 2016, 13 pages.
Anderson, K. et al., *Microfluidic-Based Measurements of Cytochrome P450 Enzyme Activity of Primary Mammalian Hepatocytes,* Analyst, 135 (2010) 1282-1287.
Andrade, R. J. et al., *Assessment of Drug-Induced Hepatotoxicity in Clinical Practice: A Challenge for Gastroenterologist,* World J Gastroenterol (Jan. 21, 2007) 329-340.
Anton, E., *Delayed Toxicity of Cyclophosphamide in Normal Mice,* Br. J. exp. Path, 68 (1987) 237-249.
Baldwin, S. J. et al., *Cytochrome P450 Gene Induction in Rates Ex Vivo Assessed by Quantatative Real-Time Reverse Transcriptase-Polymerase Chain Reaction (Taqman),* Drug Metabolism and Disposition, vol. 34, No. 6 (2006) 1063-1069.
Baudoin, R. et al., *Trends in the Development of Microfluidic Cell Biochips for In Vitro Hepatotoxicity,* Toxicology In Vitro, 21 (2007) 535-544.
Blaha, J. et al., *Histology Technology and Lean Healthcare Hand in Hand,* iSixSigma (2010) 4 pages.
Bosch, T. M. et al., *Pharmacogenetic Screening of CYP3A and ABCB1 in Relation to Population Pharmacokinetics of Docetaxel,* Clin Cancer Res, 12 (19) (2006) 5786-5793.
Chen, D. et al., *An Integrated, Self-Contained Microfluidic Cassette for Isolation, Amplification, and Detection of Nucleic Acids,* Biomed Microdevices, 12 (2010) 705-719.
Chow, S. C. et al., *Design and Analysis of Animal Studies in Pharmaceutical Development,* Taylor & Francis (1998) p. 36.
Gulliksen, A. et al., *Towards a "Sample-In, Answer-Out" Point-of-Care Platform for Nucleic Acid Extraction and Amplification: Using an HPV E6/E7 mRNA Model System,* Journal of Oncology, vol. 212, Art. ID 905024 (2012) 12 pages.
Hagan, K. A. et al., *An Integrated, Valveless System for Microfluidic Purification and Reverse Transcription-PCR Amplification of RNA for Detection of Infectious Agents,* Lap Chip, 11 (2011) 957-961.
Hattersley, S. M. et al., *Development of a Microfluidic Device for the Maintenance and Interrogation of Viable Tissue Biopsies,* Lab Chip, 8 (2008) 1842-1846.
Ho, J. et al., *Use of Contextual Inquiry to Understand Anatomic Pathology Workflow: Implications for Digital Pathology Adoption,* J Pathol Inform (2012) 10 pages.
Jadaho, S. B. et al., *Murine Alanine Aminotransferase: cDNA Cloning, Functional Expression, and Differential Gene Regulation in Mouse Fatty Liver,* Hepatology (May 2004) 1297-1302.
Jiang, G. et al., *mRNA Isolation in a Microfluidic Device for Eventual Integration of cDNA Library Construction,* Analyst, 125 (2000) 2176-2179.
Kouadjo, K. E. et al., *Housekeeping and Tissue-Specific Genes in Mouse Tissues,* BMC Genomics, 8:127 (2007) 16 pages.
Lia, M. et al., *Chromosomal Deletions Around the Albino Locus in the Mouse Cause Loss of Hormone-Inducible Expression of the Unlinked Structural Gene Encoding Cytosolic Aspartate Aminotransferase,* Proc. Natl.Acad. Sci, vol. 92 (Jan. 1995) 788-790.
Lim, G. S. et al., *A Lab-on-a-Chip System Integrating Tissue Sample Preparation and Multiplex RT-qPCR for Gene Expression Analysis in Point-of-Care Hepatotoxicity Assessment,* Lab Chip, 15 (2015) 4032-4043.
Liu, D., *Handbook of Nucleic Acid Purification,* CRC Press (2009) pp. 33-34.
Liu, H. B. et al., *Micro Air Bubble Formation and Its Control During Polymerase Chain Reaction (PCR) in Polydimethylsiloxane (PDMS) Microreactors,* J. Micromech. Microeng., 17 (2007) 2055-2064.
Liu, R. H. et al., *Self-Contained, Fully Integrated Biochip for sample Preparation, Polymerase Chain Reaction Amplification, and DNA Microarray Detection,* Anal. Chem., 76 (2004) 1824-1831.
McPherson, M. et al., *PCR,* Second Edition, Taylor & Francis (2006) (2007 e-book version) pp. 34, 36.
Mohan, R. et al., *Design Considerations for Elastomeric Normally Closed Microfluidic Valves,* Sensors and Actuators B, 160 (2011) 1216-1223.
Oblath, E. A. et al., *A Microfluidic Chip Integrating DNA Extraction and Real-Time PCR for the Detection of Bacteria in Saliva,* Lab Chip, 13 (2013) 1325-1332.
Pernagallo, S. et al., *Novel Biochip Platform for Nucleic Acid Analysis,* Sensors, 12 (2012) 8100-8011.
Ramalingam, N. et al., *Real-Time PCR Array Chip With Capillary-Driven Sample Loading and Reactor Sealing for Point-of-Care Applications,* Biomed Microdevices, 11 (2009) 1007-1020.
Ramalingam, N. et al., *Real-Time PCR-Based Microfluidic Array Chip for Simultaneous Detection of Multiple Waterborne Pathogens,* Sensors and Actuators B, 145 (2010) 543-552.
Reboucas, E. D. L. et al., *Real-Time PCR and Importance of Housekeepings Genes for Normalization and Quantification of mRNA Expression in Different Tissues,* Braz. Arch. Biol. Technol., vol. 56, No. 1 (2013) 143-154.

(56) References Cited

OTHER PUBLICATIONS

Reagan, W. J. et al., *Metabolic Adaptive ALT Isoenzyme Response in Livers of C57/BL6 Mice Treated With Dexamethasone*, Toxicologic Pathology, 40 (2012) 1117-1127.

Roth, A. et al., *Gene Expression-Based In Vivo and In Vitro Prediction of Liver Toxicity Allows Compound Selection at an Early Stage of Drug Development*, J Biochem Molecular Toxicology, vol. 25, No. 3 (2011) 183-194.

Santrach, P. J., *Current & Future Applications of Point of Care Testing*, Mayo Clinic, (slide presentation) (undated) (www.cdc.gov) 31 pages.

Sayers, M. B. et al., *A Real-Time Continuous Flow Polymerase Chain Reactor for DNA Expression Quantification*, IMECE2007-43058, 2007 ASME International Mechanical Engineering Congress and Exposition (Nov. 11-15, 2007) Seattle, Washington, USA, 7 pages.

Shaw, K. J. et al., *Integrated RNA Extraction and RT-PCR for Semi-Quantitative Gene Expression Studies on a Microfluidic Device*, Laboratory Investigation, 93 (2013) 961-966.

Sosa, L. et al., *Rescue of In Vivo FAS-Induced Apoptosis of Hepatocytes by Corticosteriods Either Associated With Alcohol Consumption by Mice or Provided Exogenously*, International Immunopharmacology, 5 (2005) 301-314.

Standish, R. A. et al., *An Appraisal of the Histophathological Assessment of Liver Fibrosis*, Gut, 55 (2006) 569-578.

Vakharia, D. D. et al., *Effect of Metals on Polycyclic Aromatic Hydrocarbon Induction of CYP1A1 and CYP1A2 in Human Hepatocyte Cultures*, Toxicology and Applied Pharmacology, 170 (2001) 93-103.

Van Heirstraeten, L. et al., *Integrated DNA and RNA Extraction and Purification on an Automated Microfluidic Cassette From Bacterial and Viral Pathogens Causing Community-Acquired Lower Respiratory Tract Infections*, Lab Chip, 14 (2014) 1519-1526.

Van Midwoud, P. M. et al., *Microfluidic Devices for In Vitro Studies on Liver Drug Metabolism and Toxicity*, Integr. Biol., 3 (2011) 509-521.

Wit, E. et al., *Statistics for Microarrays: Design, Analysis and Inference*, Wiley & Sons (2004), p. 37.

Xia, H. M. et al., *Aeroelasticity-Based Fluid Agitation for Lab-On-Chips*, Lab Chip, 13 (2013) 1619-1625.

Xia, H. M. et al., *Converting Steady Laminar Flow to Oscillatory Flow Through a Hydroelasticity Approach at Microscales*, Lab Chip, 12 (2012) 60-64.

Xiang, Q. et al., *Real Time PCR on Disposable PDMS Chip With a Miniaturized Thermal Cycler*, Biomedical Microdevices, 7:4 (2005) 273-279.

Zhang, C. et al., *PCR Microfluidic Devices for DNA Amplification*, Biotechnology Advances, 24 (2006) 243-284.

Zhang, C. et al., *Miniaturized PCR Chips for Nucleic Acid Amplification and Analysis: Latest Advances and Future Trends*, Nucleic Acids Research, vol. 35, No. 13 (2007) 4223-4237.

Zhang, Y. et al., *An All-in-One Microfluidic Device for Parallel DNA Extraction and Gene Analysis*, Biomed Microdevices, 12 (2010) 1043-1049.

\* cited by examiner a)

b)
Final-Primer Concentrations Against Signal Intensities

TESTING DEVICE, MICROFLUIDIC CHIP AND NUCLEIC ACID TESTING METHOD

CROSS-REFERENCE TO RELATED APPLICATIONS

The present application is a national phase entry of PCT/SG2016/050116, filed on 14 Mar. 2016, which claims the benefit of the U.S. provisional patent application No. 62/133,014 filed on 13 Mar. 2015, the entire contents of which are incorporated herein by reference for all purposes.

TECHNICAL FIELD

Embodiments relate generally to testing device, microfluidic chip and nucleic acid testing method.

BACKGROUND

Over the last decade, research and development for point-of-care testing (POCT) and clinical diagnostic systems for personalized healthcare based on lab-on-a-chip (LOC) microfluidic technologies have increased significantly. However, a real wanting need still remains to date for an easy-to-use POCT device that is able to perform rapid (substantially above what conventional devices provides), on-the-spot diagnostic tests for a wide variety of disease detection and toxicity assessment. This may be due to inherent complexities associated with traditional diagnostic methods which are largely incompatible to be applied in POCT devices.

For example, in the area of liver assessment for liver disease classification and hepatotoxicity, the traditional methods for liver assessment often require trained personnel, multistep procedures, and complex logistics, including requiring multiple tools and equipment, and considerable amount of processing/administrative time, thus rendering them incompatible with POCT device.

On the other hand, microfluidic technology and LOC devices, such as those disclosed in US Patents Applications Nos. 2014/0038193, US2011/0207140, 2010/0297640 and US 2010/0159582, are established technology, with applications in rapid, accurate medical diagnostics to meet the needs of personalized medicine. In the research domain, LOC devices have also been developed for a variety of diagnostic and analytical functions, as such analytical chemistry, pathogen or disease detection, as well as identification of environmental pollutants. However, the microfluidic technology and devices remain rudimentary as they largely embody only semi-quantitative or single sample/gene detection capabilities. For example, in the area of liver assessment, there is no LOC reported which is suitable for application in POCT device.

Example embodiments provide testing device, microfluidic chip and nucleic acid testing method that seek to address at least some of the issues identified above.

SUMMARY

According to various embodiments, there is provided a testing device including a capturing tool and a microfluidic chip having a plurality of chambers connected in a network, a sample receiving port connected to the network, and a guide structure configured to receive the capturing tool, wherein the capturing tool is configured to capture sample in a distal position from the guide structure and further configured to transfer captured sample to the sample receiving port in a proximal position from the guide structure.

According to various embodiments, there is provided a microfluidic chip including a plurality of chambers connected in a network, a sample receiving port connected to the network, and a guide structure configured to receive a capturing tool, wherein the capturing tool is configured to capture sample in a distal position from the guide structure and further configured to transfer the captured sample to the sample receiving port in a proximal position from the guide structure.

According to various embodiments, there is provided a testing device comprising a frame structure configured to receive a microfluidic chip as described herein.

According to various embodiments, there is provided a method for determining a target messenger RNA (mRNA) in a tissue using the test device or microfluidic chip disclosed herein, the method comprising the steps of (a) transferring a sample that has been obtained using a capture tool to a sample receiving port; (b) extracting RNA from the captured sample within the test device or microfluidic chip; and (c) determining the target mRNA by quantitative real-time reverse transcription polymerase chain reaction (real-time RT-PCR).

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION

Embodiments described below in context of the apparatus are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "lateral", "side", "up", "down" etc., when used in the following description are used for convenience and to aid understanding of relative positions or directions, and not intended to limit the orientation of any device, or structure or any part of any device or structure. In addition, the singular terms "a," "an," and "the" include plural referents unless context clearly indicates otherwise. Similarly, the word "or" is intended to include "and" unless the context clearly indicates otherwise. The term "comprises" means "includes."

Various embodiments relate to a general point-of-care testing (POCT) biological tissue assessment device, realized as a "Lab-in-a-Needle", and embody a method of using microfluidic Nucleic Acid Testing (NAT) for sample preparation, nucleic acid amplification, and nucleic acid detection for POCT. Various embodiments of the device and testing method are illustrated in the following. Various examples of the device and testing method are also illustrated by means as an application to liver assessment.

Figure 1A:
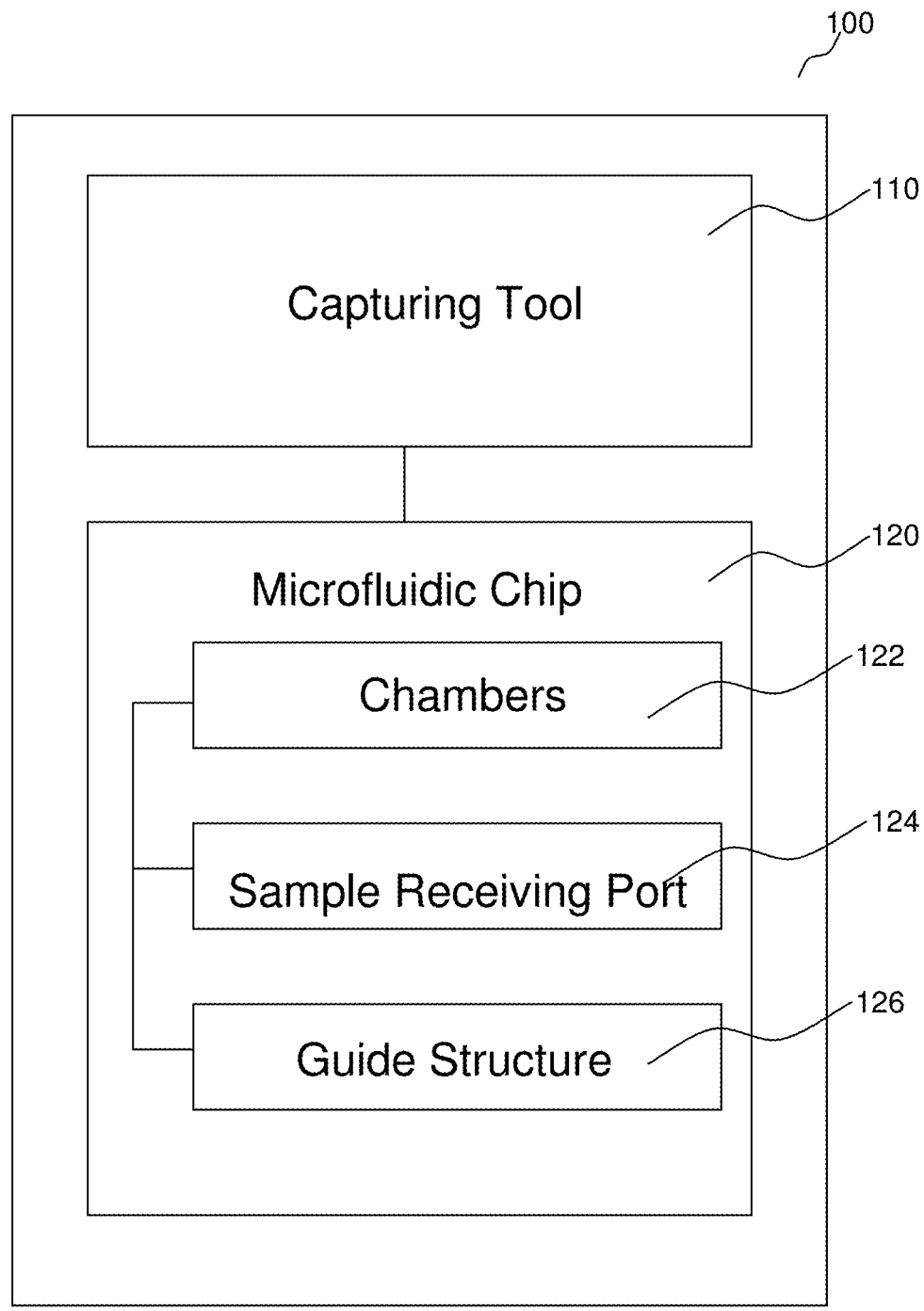
FIG. 1A shows a schematic block diagram of a testing device according to various embodiments.

FIG. 1A shows a schematic block diagram of a testing device 100 according to various embodiments. The testing device 100 may be a POCT device for performing diagnostic tests, including disease detection and toxicity assessment. The testing device 100 may include a capturing tool 110 and a microfluidic chip 120. The capturing tool 110 may serve as a puncture and penetration tool and as means to capture sample for subsequent analysis. Accordingly, the capturing tool 110 may be configured to capture sample. The captured sample may include tissue, biofluid, blood, plasma, saliva, urine, etc. The capturing tool 110 may be used to remove a sample of tissues in a manner similar to the removal of tissues in a biopsy procedure. The capturing tool 110 may include a capturing element 112 configured to capture, extract and/or remove sample from a target location of a body. According to various embodiments, the capturing tool 110 may be in the form of a biopsy needle or a hypodermic needle. The microfluidic chip 120 may serve as a lab-on-chip (LOC) platform for performing diagnostic of the sample captured by the capturing tool 110. For example, the microfluidic chip 120 may be configured to perform either one or any combination of sample preparation, nucleic acid amplification and nucleic acid detection. Sample preparation may include tissue and cellular lysis, mRNA extraction and/or mRNA purification. Nucleic acid amplification may include polymerase chain reaction (PCR) or reverse transcription polymerase chain reaction (RT-PCR). Nucleic acid detection may include fluorescence detection of amplified cDNA.

According to various embodiments, the microfluidic chip 120 may include a plurality of chambers 122 connected in a network, a sample receiving port 124 connected to the network and a guide structure 126 configured to receive the capturing tool 110. The capturing tool 110 may be configured to capture sample in a distal position from the guide structure 126 and further configured to transfer the captured sample to the sample receiving port 124 in a proximal position from the guide structure 126.

Accordingly, the guide structure 126 may serve as a contact point between the capturing tool 110 and the microfluidic chip 120. The capturing tool 110 may simply rest, sit or place in the guide structure 126 of the microfluidic chip 120, i.e. the capturing tool 110 may not be bound, fastened or secured to the microfluidic chip 120. The capturing tool 110 may also be connected, joined or coupled to the guide structure 126 such that the capturing tool 110 may be bound, fastened or secured to the microfluidic chip 120.

According to various embodiments, the capturing tool 110 may include the capturing element 112. The capturing element 112 of the capturing tool 110 may be movable relative to the guide structure 126. The capturing element 112 may be configured to capture sample in a distal position from the guide structure 126 and further configured to transfer the captured sample to the sample receiving port 124 in a proximal position from the guide structure 126. The capturing tool 110 may be received on the guide structure 126 of the microfluidic chip 120 such that the capturing element 112 of the capturing tool 110 may be moved relative to the guide structure 126. The capturing element 112 may be moved to a distal position situated away from the guide structure 126. In the distal position, the capturing tool 110 may be operated such that the capturing element 112 may capture, extract and/or remove sample from a target location of a body. The capturing element 112 may then be moved to a proximal position situated near or at the guide structure 126. In the proximal position, the capturing tool 110 may be operated for the capturing element 112 to transfer the captured sample to the sample receiving port 124. The capturing element 112 may be configured to passively transfer the captured sample. According to various embodiments, the capturing element 112 may include non-stick coating to facilitate passive transfer of the sample to the sample receiving port 124.

Figure 1B:
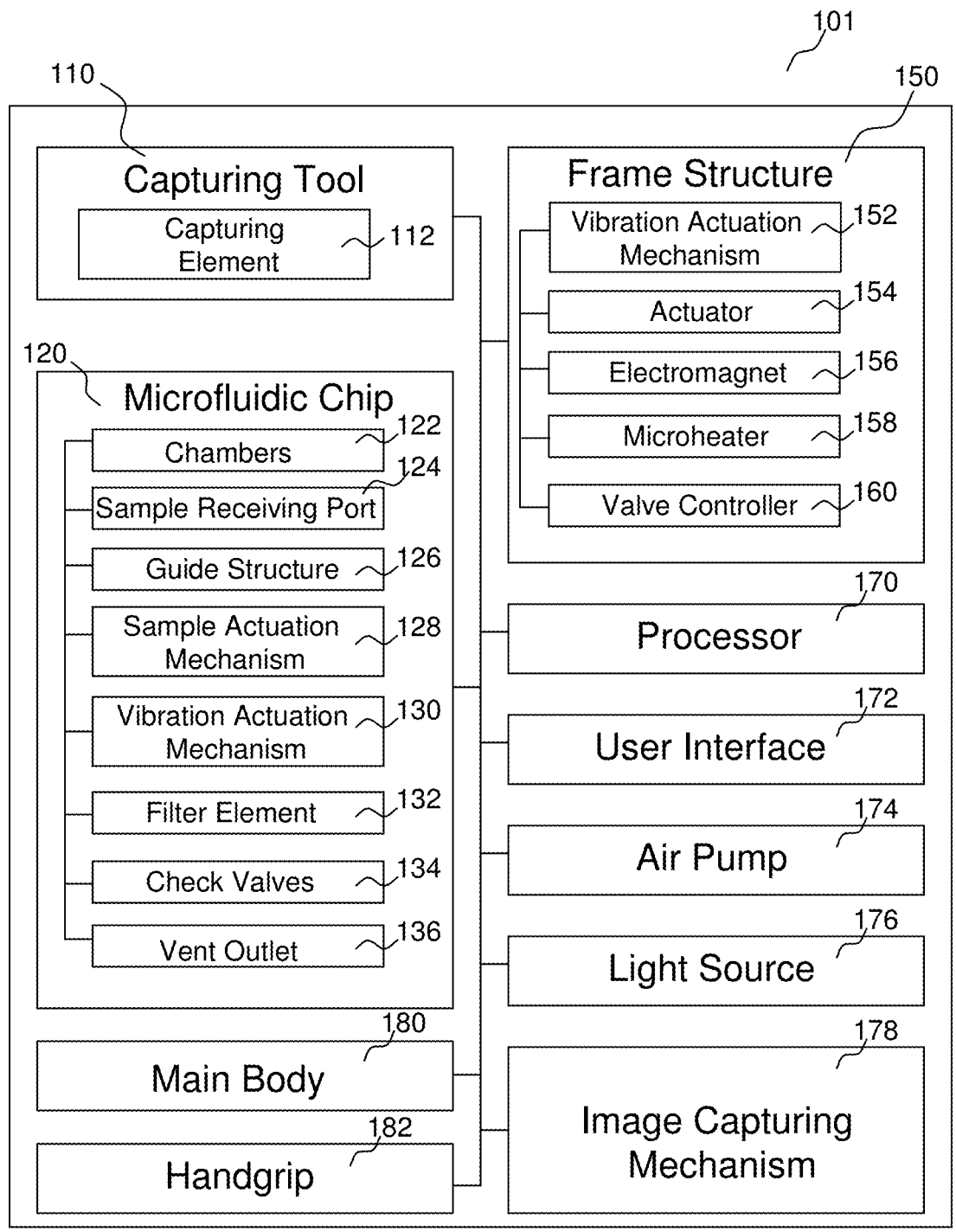
FIG. 1B shows a schematic block diagram of a testing device according to various embodiments.

FIG. 1B shows a schematic block diagram of a testing device 101 according to various embodiments. Similar to the testing device 100 in FIG. 1A, the testing device 101 may include a capturing tool 110 and a microfluidic chip 120. The microfluidic chip 120 may include a plurality of chambers 122 connected in a network, a sample receiving port 124 connected to the network, and a guide structure 126 configured to receive the capturing tool 110. The capturing tool 110 may be configured to capture sample in a distal position from the guide structure 126 and further configured to transfer captured sample to the sample receiving port 124 in a proximal position from the guide structure 126.

According to various embodiments, the capturing tool 110 may include a capturing element 112. The capturing element 112 of the capturing tool 110 may be movable relative to the guide structure 126.

According to various embodiments, the guide structure 126 of the microfluidic chip 120 may be configured to facilitate the transfer of sample from the capturing tool 110 to the sample receiving port 124 of the microfluidic chip 120. According to various embodiments, the guide structure 126 may include a wall structure 426a (see FIG. 9) protruding from a surface of the microfluidic chip 120. The wall structure 426a may be configured to protrude from the surface of the microfluidic chip in the vicinity of an edge of the sample receiving port 124. In an implementation, the wall structure may include elevated sidewalls. Accordingly, the wall structure 426a may serve to direct the sample towards the sample receiving port 124.

According to various embodiments, the capturing tool 110 may be a needle. The needle may be a biopsy needle. Accordingly, the guide structure 126 may be configured to receive the needle such that a longitudinal axis of the needle may be substantially parallel to the surface of the microfluidic chip 120. In this arrangement, a portion of the needle's length may be received on the guide structure 126 such that the longitudinal axis of the needle may be substantially parallel to the surface of the microfluidic chip 120. Accordingly, a tip of the needle may be situated in the distal position from the guide structure 126. According to various embodiments, the portion of the needle's length received on the guide structure may include an opening to allow the transfer of the sample from the needle to the sample receiving port 124. According to various embodiments, when the capturing tool 110 is a biopsy needle, the capturing element 112 may be a notch on an inner stylet of the biopsy needle, which is movable along the cutting cannula of the biopsy needle.

According to various embodiments, the microfluidic chip 120 may further include sample actuation mechanism 128 connected to the sample receiving port 124. The sample actuation mechanism 128 may be configured to move the sample from the sample receiving port 124 to at least one of the plurality of chambers 122 of the microfluidic chip 120. In an implementation, the sample actuation mechanism 128 may include an airflow inlet which may provide a flow of air to move the sample from the sample receiving port 124 to at least one of the plurality of chambers 122. The airflow inlet may be further connected to an air pump or an air source which may generate the flow of air for moving the sample.

According to various embodiments, the microfluidic chip 120 may further include a vibration actuation mechanism 130 at the sample receiving port 124. The vibration actuation mechanism 130 may be configured to cause lysis of the sample received in the sample receiving port 124. The vibration actuation mechanism 130 may cause lysis via vibrational shearing of the sample. According to various embodiments, the vibration actuation mechanism 130 may include a silica-sand coated piezoelectric disk embedded at the base of the microfluidic chip 120. According to various embodiments, the vibration actuation mechanism 130 may include a flexible and deformable thin film silica membrane.

According to various embodiments, the microfluidic chip 120 may further include a filter element 132. The sample receiving port 124 may be connected to the network of the plurality of chambers 122 via the filter element 132. After the sample has undergone lysis in the sample receiving port 124, the lysate may be moved to one of the plurality of chambers 122. The sufficiently broken down sample may be moved by the sample actuation mechanism 128 through the filter element 132. The filter element 132 may be configured to remove excessively large pieces of samples that remain after the lysis. The filter element 132 may include filtration micro-pillars. The filtration micro-pillars may be made from polycarbonate or poly(methyl methacrylate) using micro-milling, hot embossing or injection molding fabrication techniques.

According to various embodiments, the microfluidic chip 120 may further include a plurality of check valves 134 interspersed in the network. The plurality of check valves 134 may be configured to allow sample, fluids, liquid or liquid mixture to flow in one direction from one chamber to another so that backflow is prevented when sample, fluids, liquid or liquid mixture moves from one chamber to another. According to various embodiments, a check valve 134 may be connected to the filter element 132 such that after the sample has passed through the filter element 132, the sample may pass through the check valve 134 into a first chamber of the plurality of chambers 122. The check valve 134 may prevent backflow of the sample from the first chamber of the plurality of chambers 122.

According to various embodiments, at least one of the plurality of chambers 122 of the microfluidic chip 120 may include a plurality of microbeads. The plurality of microbeads may include a plurality of magnetic microbeads. According to various embodiments, the plurality of microbeads may be preloaded in the at least one of the plurality of chambers 122. According to various embodiments, the plurality of magnetic microbeads are suited for immobilizing thereon total RNA, total mRNA or a plurality of selected mRNAs comprising the target mRNA and the endogenous control mRNA, by functionalization with capture moieties. Suitable capture moieties may be any nucleic acid sequences and may comprise oligo-dT (to capture polyadenylated mRNA), random hexamers (or longer random motifs; to capture total RNA) or gene-specific sequences. According to various embodiments, the at least one of the plurality of chambers 122 may be the first chamber of the plurality of chambers 122 in communication with the sample receiving port 124. The first chamber of the plurality of chambers 122 may be a mixing chamber. The mixing chamber may be configured to cause the lysate and the plurality of microbeads to mix based on vibrational-based mixing. The mixing chamber may include flexible and deformable thin-film silica membrane capable of being set into vibration by piezoelectric means. The mixing chamber may also be configured to actively maintain the microbeads within the mixing chamber. The magnetic microbeads may be kept within the mixing chamber via an electromagnet attracting the magnetic microbeads. The electromagnet may be external to the mixing chamber.

According to various embodiments, at least one of the plurality of chambers 122 of the microfluidic chip 120 may include a flexible deformable element. The flexible deformable element may include the flexible and deformable thin-film silica membrane.

According to various embodiments, at least one of the plurality of chambers 122 may be pre-loaded with liquid. According to various embodiments, the liquid may include either one or a mixture of liquids selected from the group consisting of buffer solution, reagent or fluorescence dye.

According to various embodiments, the at least one of the plurality of chambers 122 containing buffer solution may be a buffer solution reservoir chamber. The buffer solution reservoir chamber may be connected to the mixing chamber via a check valve 134. According to various embodiments, the microfluidic chip 120 may include two or more buffer solution reservoir chambers. According to an implementation, the microfluidic chip 120 may include four buffer solution reservoir chambers. Each of the buffer solution reservoir chambers may contain buffer solution selected from the group consisting of lysis/binding buffer, washing buffer A, washing buffer B, and elution buffer. The buffer solution reservoir may include a flexible thin film membrane. The buffer solution in the buffer solution reservoir chamber may be actuated to flow into the mixing chamber via an actuator configured to deform the flexible thin film membrane. The actuator may include linear actuators or a plunger actuated pump. When there are more than one buffer solution reservoir chambers, the respective chambers may be actuated in a predetermined sequence for flowing into the mixing chamber to mix with the lysate, and the microbeads. mRNA from the sample may hybridize onto the microbeads as a result of the mixing in the mixing chamber.

According to various embodiments, at least one of the plurality of chambers 122 may be a waste reservoir chamber. The waste reservoir chamber may be in communication with the mixing chamber. Unwanted tissue/cellular contaminants and unwanted buffer solutions may be actuated to flow into the waste reservoir chamber.

According to various embodiments, the at least one of the plurality of chambers 122 containing reagent and/or dye may be an amplification mixing chamber. The amplification mixing chamber may be in communication with the mixing chamber. Between the amplification mixing chamber and mixing chamber, there may be an elution chamber and a microbeads capture chamber. From the mixing chamber, microbeads carrying the hybridized mRNA and elution buffer solution may be actuated to flow into the elution chamber. The elution chamber may be configured to heat up and maintain at a predetermined temperature so that the hybridized mRNA may be released into the solution. The elution chamber may be heated up via an external heat source. For example, a microheater may be provided to heat up the elution chamber. After the hybridized mRNA is released into the solution, the microbeads and the solution may be flowed through the microbeads capture chamber. The microbeads capture chamber may be configured to hold the microbeads in the microbeads capture chamber while the solution may flow through the microbeads capture chamber into the amplification mixing chamber. The magnetic microbeads may be held in the microbeads capture chamber via an electromagnet attracting the magnetic microbeads. The electromagnet may be external to the microbeads capture chamber.

According to various embodiments, the amplification mixing chamber may be configured to cause mixing of the mRNA and the reagent via vibrational-based mixing. The mixing chamber may include flexible and deformable thin-film silica membrane capable of being set into vibration by piezoelectric means.

According to various embodiments, at least one of the pluralities of chambers 122 is pre-loaded with a set of PCR primers. The at least one of the plurality of chambers 122 containing primers may be an amplification reaction chamber. The amplification reaction chamber may be connected to the amplification mixing chamber via a check valve. There may be multiple amplification reaction chamber pre-loaded with different sets of primers. The amplification reaction chamber may be configured to allow nucleic acid detection. Nucleic acid detection may be via fluorescence detection. Fluorescence detection may be via a camera module. The camera module may be external to the amplification reaction chamber.

According to various embodiments, the microfluidic chip 120 may further include a vent outlet 136 connected to the network of the plurality of chambers 122. The vent outlet 136 may be configured to aid in the specific flow and actuation of sample/fluid/solution through the different chambers and components of the microfluidic chip 120. There may be multiple vent outlets 136 connected to various points in the network of the plurality of chambers 122.

According to various embodiments, the testing device 101 may include a frame structure 150 configured to receive the microfluidic chip 120. The frame structure 150 may be configured to be integrated with the external actuators, motors, valve controllers, electromagnetic source, heat source etc. as required by the various chambers 122 of the microfluidic chip 120.

According to various embodiments, the frame structure 150 may include a vibration actuation mechanism 152. The vibration actuation mechanism 152 may be located on the frame structure 150 such that when the microfluidic chip 120 is received on the frame structure 150, the vibration actuation mechanism 152 may provide the necessary actuation to the sample receiving port as well as the mixing chamber and the amplification mixing chamber of the microfluidic chip 120. The vibration actuation mechanism 152 may include silica-sand coated piezoelectric-based actuation mechanism, vibration-based mixing actuation mechanism, etc.

According to various embodiments, the frame structure 150 may include an actuator 154. The actuator 154 may be configured to actuate buffer solution reservoir chamber to flow the buffer solution into the mixing chamber. The actuator 154 may compress and/or deform the flexible thin-film membrane of the buffer solution reservoir chamber to cause the buffer solution to flow. The actuator 154 may be located on the frame structure 150 such that when the microfluidic chip 120 is received on the frame structure 150, the actuator 154 may provide the necessary actuation to the buffer solution reservoir chamber of the microfluidic chip 120. The actuator 154 may include plunger-actuated pump using linear motor actuators built into the frame structure 150.

According to various embodiments, the frame structure 150 may include an electromagnet 156. The electromagnet 156 may be configured to maintain the magnetic microbeads within the mixing chamber of the microfluidic chip 120 during mixing and/or to capture the magnetic microbeads when the magnetic microbeads is flowing through the microbeads capture chamber of the microfluidic chip 120. The electromagnet 156 may be located on the frame structure 150 such that when the microfluidic chip 120 is received on the frame structure 150, the electromagnet 156 may provide the necessary magnetic attraction force to the mixing chamber and the microbeads capture chamber of the microfluidic chip 120.

According to various embodiments, the frame structure 150 may include a microheater 158. The microheater 158 may be configured to provide the heat required for heating up and maintaining the temperature of the elution chamber of the microfluidic chip 120. The microheater 158 may be located on the frame structure 150 such that when the microfluidic chip 120 is received on the frame structure 150, the microheater 158 may provide the necessary heating to the elution chamber of the microfluidic chip 120.

According to various embodiments, the frame structure 150 may include a valve controller 160. The valve controller 160 may be configured to control the operation of the plurality of check valves 134 of the microfluidic chip 120. The valve controller 160 may be located on the frame structure 150 and connected to the plurality of check valves 134 such that when the microfluidic chip 120 is received on the frame structure 150, the valve controller 160 may control the operation of the check valves 134 of the microfluidic chip 120.

According to various embodiments, the testing device 101 may further include a processor 170 connected to the frame structure. The processor 170 may be configured to control the functions of the various components on the frame structure 150. According to various embodiments, the processor 170 may be a microcontroller.

According to various embodiments, the testing device 101 may further include a user interface 172 connected to the processor 170. The user interface 172 may be a display, such as an LCD display. The display may serve to display the basic operation of the testing device 101 and associated information. The display may also serve as an interactive interface for the user to provide inputs or controls functions of the testing device 101. The interactive interface may be in the form of touchscreen functions.

According to various embodiments, the user interface 172 may include an optoelectronics readout. The optoelectronics readout may provide a readout of the testing results of the microfluidic chip 120 in the testing device 101 for the user to receive instantaneous feedback on the testing.

According to various embodiments, the testing device 101 may include an air pump 174 connectable to the microfluidic chip. The air pump 174 may serve as the air flow generation mechanism for providing air flow to the sample actuation mechanism 128 to move the sample through the various components of the microfluidic chip 120.

According to various embodiments, the testing device 101 may further include a light source 176 configured to provide excitation to at least one of the plurality of chambers 122 of the microfluidic chip 120. The light source 176 may be configured to provide excitation to the amplification reaction chamber of the microfluidic chip 120 for fluorescence detection.

According to various embodiments, the testing device 101 may further include an image capturing mechanism 178. The image capturing mechanism 178 may be configured to capture excitation of fluorescent dye for fluorescence detection.

According to various embodiments, the testing device 101 may further include a main body 180 encasing the frame structure 150 and the microfluidic chip 120. The main body 180 may serve as a housing for containing the frame structure 150 and the microfluidic chip 120.

According to various embodiments, the main body 180 may be configured to receive the capturing tool 110 such that the capturing tool 110 is received on the guide structure 126 of the microfluidic chip 120 received on the frame structure 150 of the testing device 101. Accordingly, the main body 180 may include an opening for the capturing tool 110 to extend through a wall of the main body 180 such that a portion of the capturing tool 110 is within the main body 180 and received on the guide structure 126 of the microfluidic chip 120, and another portion of the capturing tool 110 is outside the main body 180.

According to various embodiments, the main body 180 may further include a main body door. The main body door may be configured to be opened/removed to access the frame structure 150 and to remove/replace the microfluidic chip 120 after use.

According to various embodiments, the testing device 101 may further include a handgrip 182 attached to the main body 180. The handgrip 182 may serve as a means to handle and manoeuvre the testing device 101 during capturing of sample with the capturing tool 110 of the testing device 101. The handgrip 182 may be configured to allow gripping and handling of the testing device 101 with the index and middle fingers. According to various embodiments, the handgrip 182 may include two rings connected to each other for gripping with the index and middle fingers.

According to various embodiments the capturing tool 110 may include a plunger. The plunger may serve as a mechanical means for operating the capturing tool 110 to capture sample from a target location in a body.

According to various embodiments, there is also provided a microfluidic chip 120. The microfluidic chip 120 may be disposable and may be suitable for one-time use. The microfluidic chip 120 may include a plurality of chambers 122 connected in a network, a sample receiving port 124 connected to the network, and a guide structure 126 configured to receive a capturing tool 110, wherein the capturing tool 110 is configured to capture sample in a distal position from the guide structure 126 and further configured to transfer the captured sample to the sample receiving port 124 in a proximal position from the guide structure 126. The capturing tool 110 may include a capturing element 112. The capturing element 112 may be movable relative to the guide structure 126.

According to various embodiments, there is provided a testing device including a frame structure 150 configured to receive a microfluidic chip 120 as described herein. The microfluidic chip 120 may be disposable such that the microfluidic chip 120 may be replaced after each use.

According to various embodiments, there is provided a "Lab-in-a-Needle" POCT diagnostic device (in other words a testing device), including the integration of an LOC microfluidic device (in other words a microfluidic chip) and an industrial-standard core biopsy needle or an industrial-standard hypodermic needle (in other words a capturing tool). Various embodiments may allow for the realization of a novel POCT device, applicable to a number of disease detection and toxicity assessment. For illustration purposes, various embodiments will be described in the following for the purpose of liver disease classification and hepatotoxicity.

Histopathology for liver assessment is largely an examination based on microscopy study on liver biopsies. It is a qualitative methodology where liver damage is based on the "determination of the degree of fibrosis and architectural change" of the extracted liver tissue. Clinical manifestations of liver failure or liver disease are often indicated by "architectural changes of the liver parenchyma" due to liver damage caused by advanced stages of liver fibrosis. At present, histological diagnosis of the degree of liver fibrosis is largely accepted as the gold standard for liver assessment in histopathology. However, the usage of histopathology in liver assessment has several critical limitations when applied to POCT.

Figure 2:
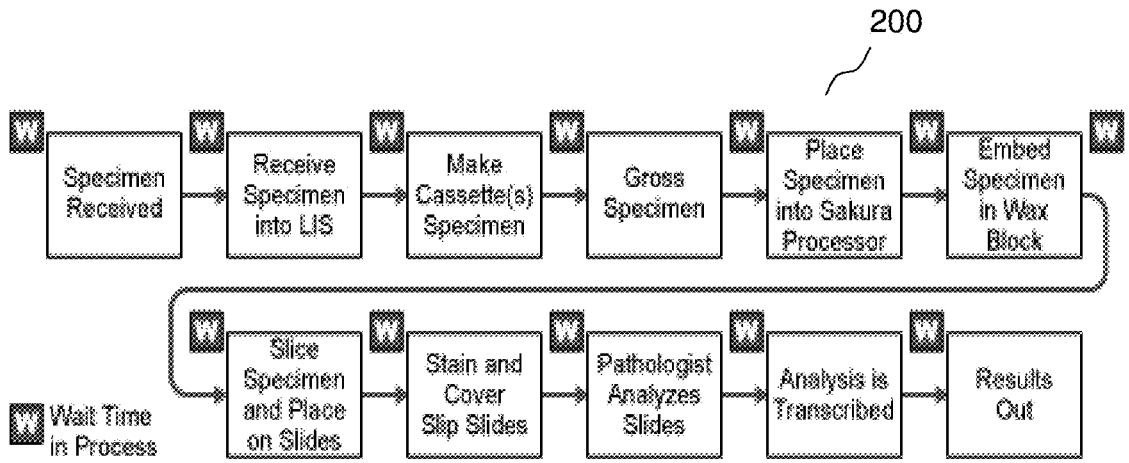
FIG. 2 shows an illustration describing a conventional histopathological process flow for a biopsied tissue sample.

FIG. 2 is an illustration describing a conventional histopathological process flow 200 for a biopsied tissue sample. Conventionally, in a histopathology process, several labour-intensive and time-consuming preparation steps are involved. Most histopathological tissue processing is usually done overnight and same-day results are generally not possible due to current technological limits. FIG. 2 shows that conventional histopathological examination often involves several required critical steps, each with their own necessary tools or equipment. Additionally, this process is largely inefficient in the sense that multiple wait time between each step is required for sample preparation.

Figure 3:
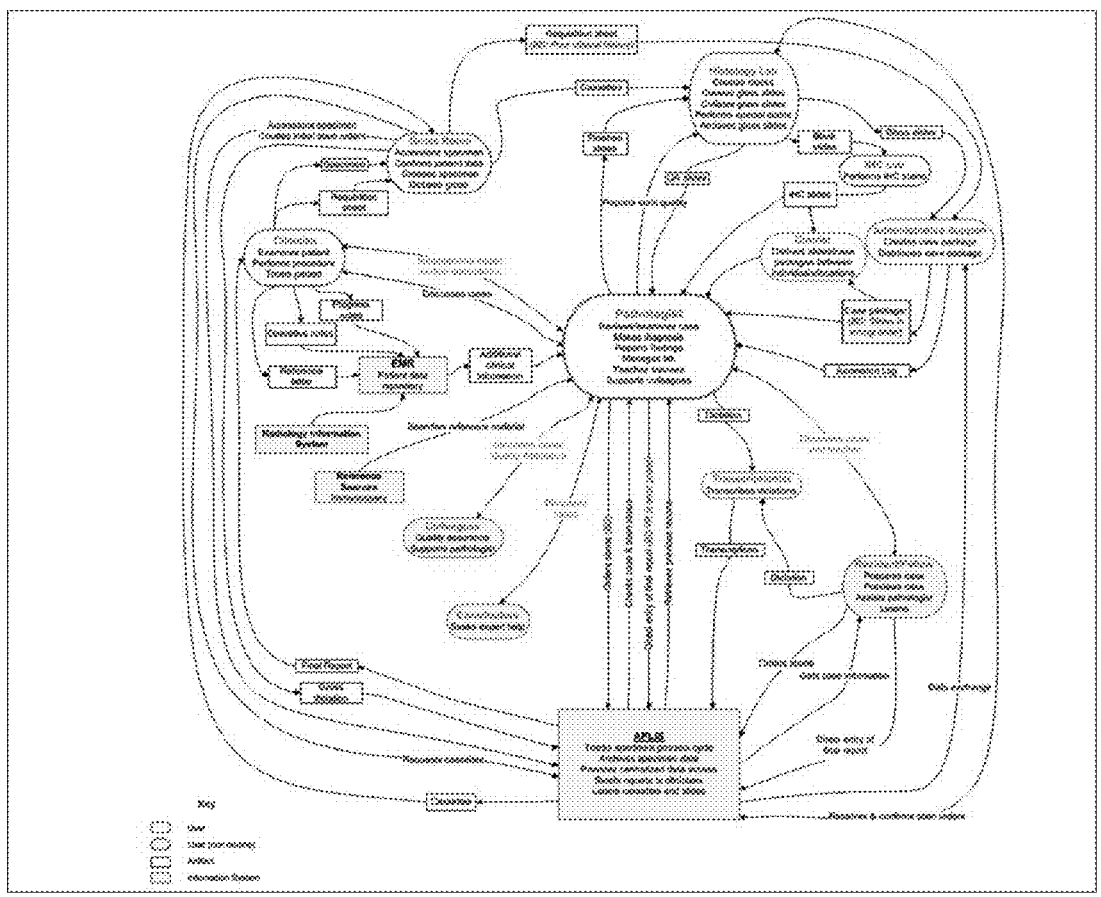
FIG. 3 shows a schematic diagram illustrating the flow of information and artifacts between all users involved in a conventional histopathological assessment.

Similarly, FIG. 3 is a schematic diagram 300 illustrating the flow of information and artifacts between all users involved in a conventional histopathological assessment. The entire diagnostic process is convoluted and complex, involving multiple trained personnel, administration and logistics. The diagnostic process typically begins with an "initiation by the clinician with the removal of a tissue specimen from the patient and terminates with the receipt of a final pathology report at the clinician's office", often taking more than a week to complete.

Figure 4:
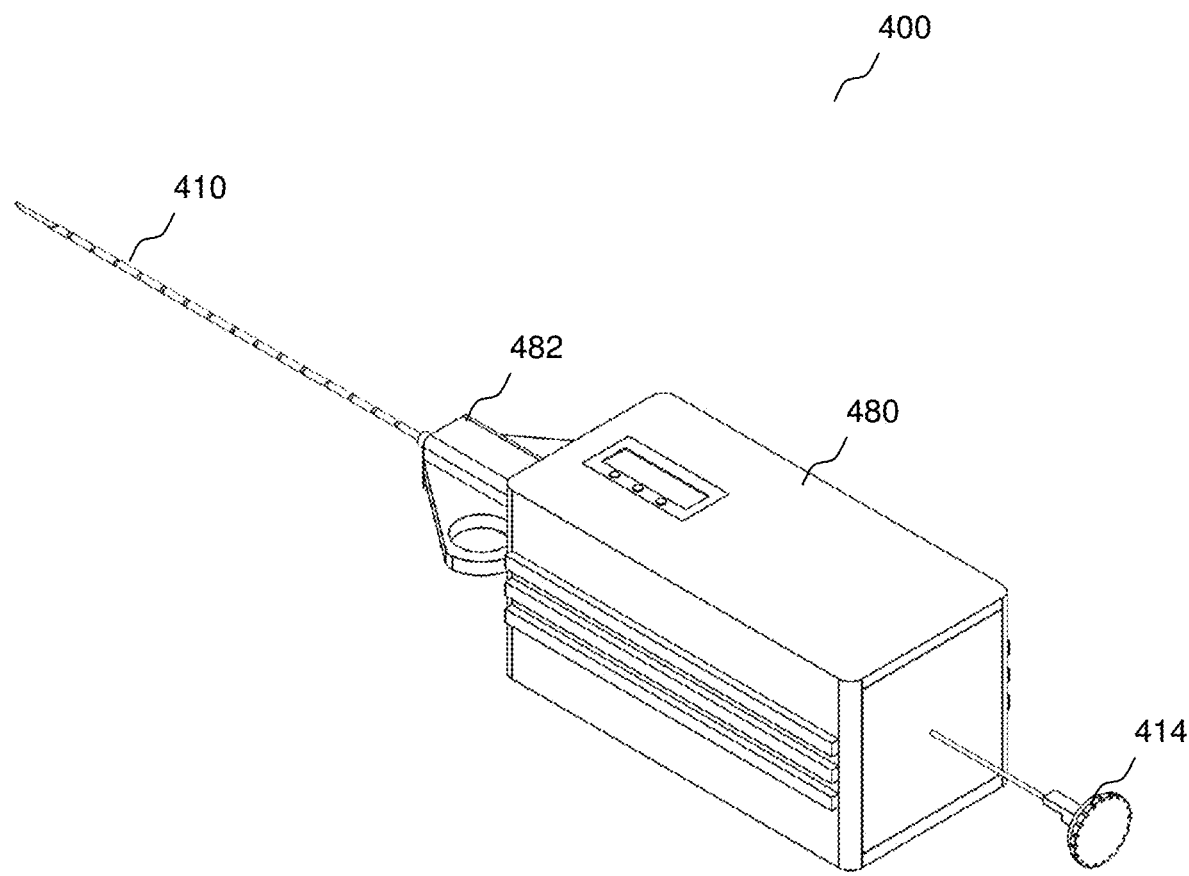
FIG. 4 shows a testing device according to various embodiments.

Various embodiments of the present invention relates to a POCT liver assessment device (in other words a testing device), termed as "Lab-in-a-Needle" 400, involving the use of microfluidic NAT for biomolecular diagnostics, such as liver toxicity assessment and liver disease classification. FIG. 4 shows the illustration of the "Lab-in-a-Needle" liver assessment device 400, embodied by an industrial-standard core biopsy needle 410 (in other words a capturing tool), a Handlegrip 482 (in other words a handgrip), a Mainbody 480, and a needle plunger 414. Accordingly, FIG. 4 shows a testing device according to various embodiments.

The industrial-standard core biopsy needle 410 may serve as a tissue puncture and penetration tool during liver biopsy and as a means to capture liver tissue for subsequent analysis. The Handlegrip 482 may serve as a means to handle and manoeuvre the entire device during liver biopsy and permits gripping and handling of the device by using both index and middle fingers. The Mainbody 480 may serve as a housing for the entire LOC microfluidic platform for the device, where microfluidic NAT would be performed on the liver tissue sample obtained by the industrial-standard core biopsy needle 410. Lastly, the needle plunger 414 may serve as a mechanical means to move the liver tissue sample from the tip of the industrial-standard core biopsy needle to the microfluidic chip 420 (FIG. 7) within the Mainbody 480.

Figure 5:
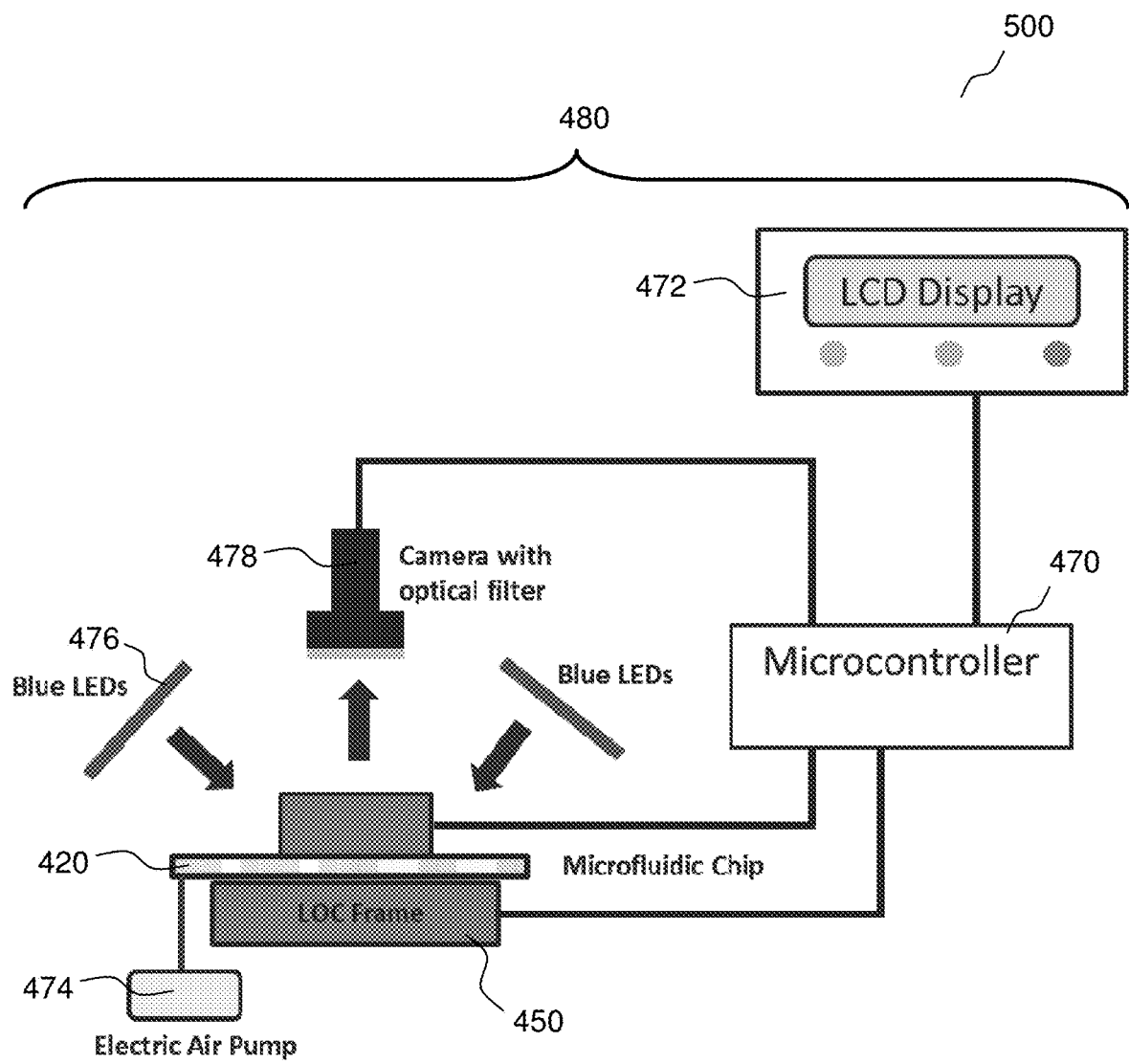
FIG. 5 shows a schematic diagram illustrating major components and their general layout embodied in a main body of the testing device of FIG. 4 according to various embodiments.

FIG. 5 shows a schematic diagram 500 illustrating the major components and their general layout embodied in the Mainbody 480 of the "Lab-in-a-Needle" device 400 according to various embodiments. Microfluidic NAT could be performed on the microfluidic chip 420, which may be made from low cost materials, such as transparent thermoplastic polymeric material, e.g. polycarbonate, poly(methyl methacrylate), or cyclic-olefin copolymer. Said microfluidic chip 420 may embody pre-loaded buffers, reagents, magnetic microbeads and primers, necessary for NAT involving sample preparation, nucleic acid amplification and nucleic acid detection. The microfluidic chip 420 may be for one-time usage and may be disposable. The microfluidic chip 420 may be swappable. Accordingly, depending on the particular proteins or nucleic acid that need to be detected, the microfluidic chip 420 in the "Lab-in-a-Needle" device 400 may be swapped such that the appropriate microfluidic chip 420 appropriate for the testing may be inserted into the "Lab-in-a-Needle" device 400. Physically, the microfluidic chip 420 may be inserted into a LOC frame 450 (in other words a frame structure) fitted for full LOC functionality. The LOC frame 450 may embody the non-disposable components of the microfluidic chip, including (but not restricted to) silica-sand coated piezoelectric-based tissue lysis component, linear motor actuators for reagents/buffers actuation, valve controls, vibration-based mixing component, electromagnets for microbeads capture and microheaters.

Figure 6:
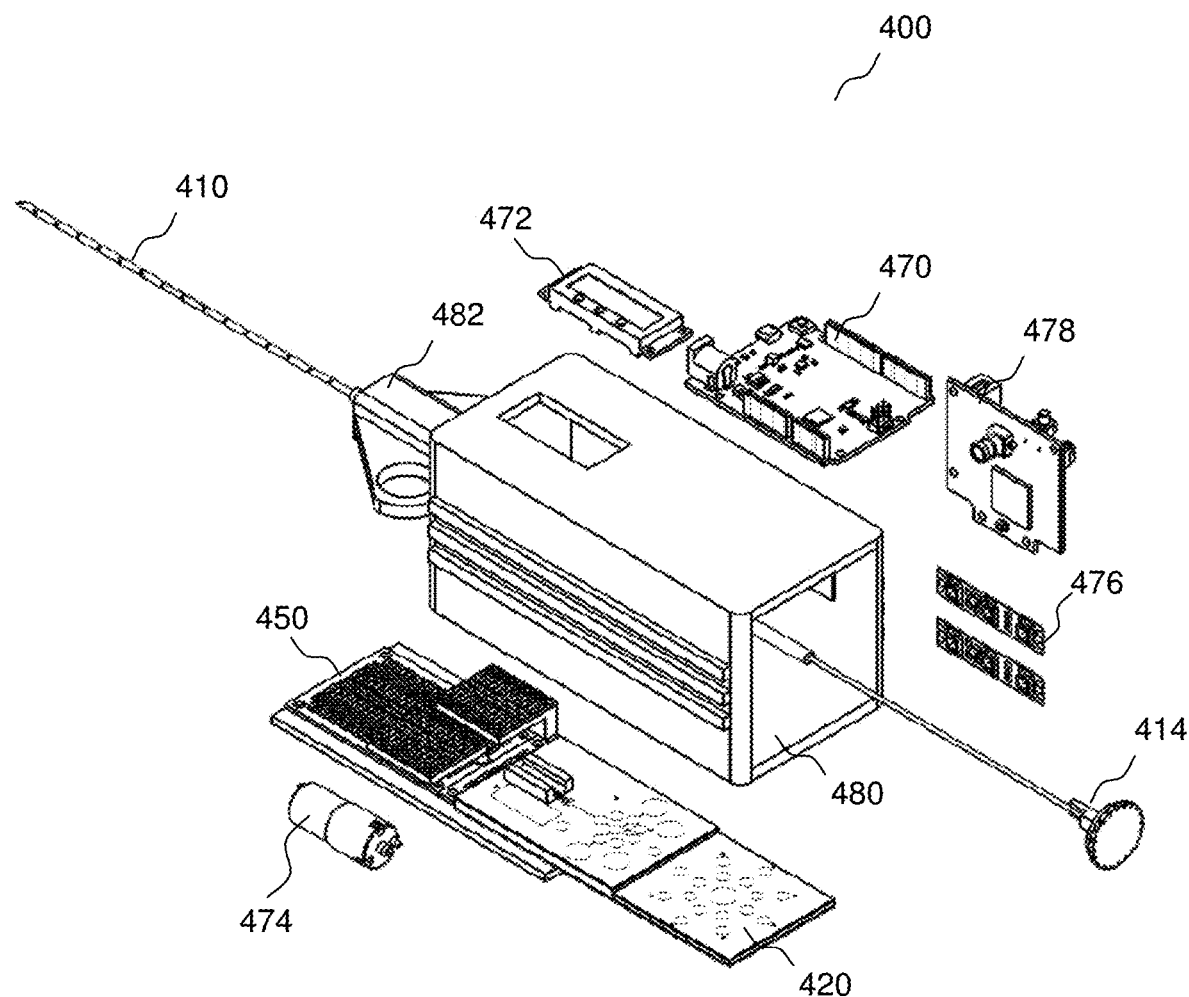
FIG. 6 shows an exploded view the testing device of FIG. 4 according to various embodiments.
Figure 7:
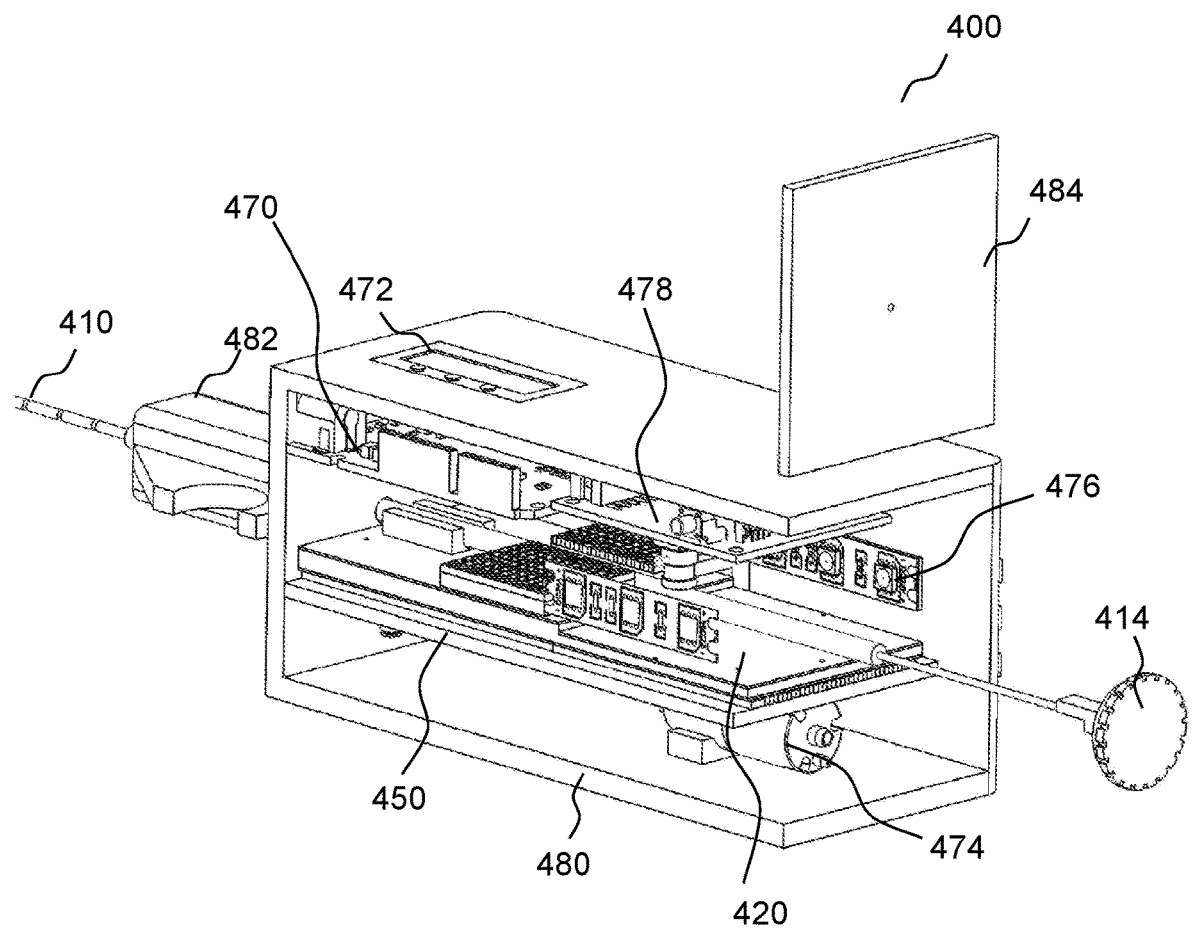
FIG. 7 shows a cut out view of the assembled the testing device of FIG. 4 according to various embodiments.

FIG. 6 shows an exploded view of the "Lab-in-a-Needle" device 400 according to various embodiments. FIG. 7 shows a cut out view of the assembled the "Lab-in-a-Needle" device 400 according to various embodiments. As shown in FIGS. 6 and 7, the LOC frame 450 may be interfaced with a microcontroller 470 (in other words a processor) for full automation. An electric air pump 202 may be included to serve as the main source of sample/fluid actuation throughout the entire microfluidic chip 420 architecture and reaction chambers, and may be connected to a sample actuation inlet 428 (FIG. 10) on the microfluidic chip 420 by means of micro-tubings. As aforementioned, the microcontroller 470 may be connected to the LOC frame 450, and serves as the control and automation of the LOC functions within the device 400, including tissue lysis, fluid/sample actuation, valve control, fluid/reagent mixing, heating and camera operation. It may also provide data to an LCD display 472 (in other words a user interface). The LCD display 472 may display the basic operation of the device and presentation of necessary information. The LCD display 472 may also serve as the main source of control of the functions of the device 400, via interactive capacitive touchscreen functions or otherwise. Blue LED arrays 476 (in other words a light source) may serve as an excitation source (~470-490 nm wavelength) for the nucleic acid fluorescence intercalating dye (preferably SYBR® Green I or EVAGREEN® dye) in reaction chambers on the microfluidic chip 420 to allow for real-time fluorescence detection. Lastly, a camera module 478 may serve as an image capturing device (connected to and controlled via the microcontroller 470) to capture fluorescence emissions from the microfluidic chip 420 in order to determine up- or down-regulation of target gene sequences from patient's liver tissue sample (comparative analysis of mRNA concentration via fluorescence emissions). The camera module 478 may be fitted with an optical bandpass filter to remove unwanted blue light coming from excitation source.

Figure 9:
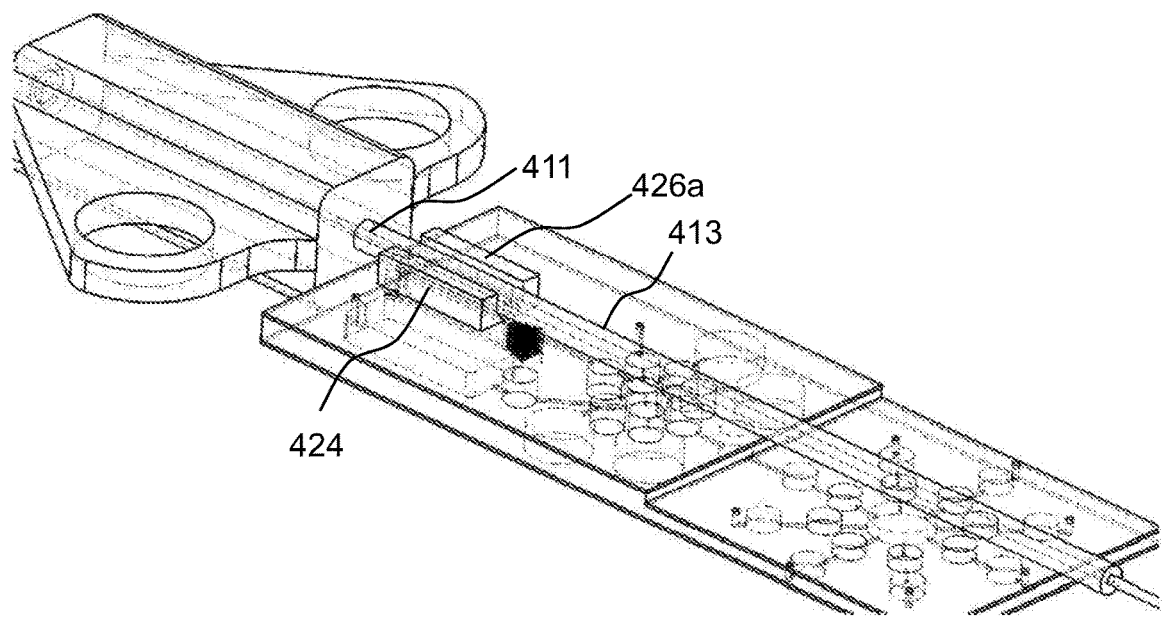
FIG. 9 shows a capturing element of the capturing tool of FIG. 8 being withdrawn to position a sample over a sample receiving port of a microfluidic chip of the testing device of FIG. 4 according to various embodiments.

FIG. 6 is an illustration of the "Lab-in-a-Needle" 400 device with aforesaid primary components depicted as unassembled. FIG. 7 is a close-up isometric view of aforementioned primary components assembled within the Mainbody 480 housing. An additional component depicted in this FIG. 7 includes the Mainbody door 484 which could be opened/removed to access the interior LOC components and to remove the disposable microfluidic chip 420 after use. As can be seen in FIG. 9, the microfluidic chip 420 may include a tissue transfer and lysis chamber 424 (in other words a sample receiving port). The tissue transfer and lysis chamber 424 may be an architecture feature in the microfluidic chip 420, which may include elevated sidewalls to aid in the transfer of liver tissue samples from the industrial-standard core biopsy needle 410 to the microfluidic chip 420.

Figure 8:
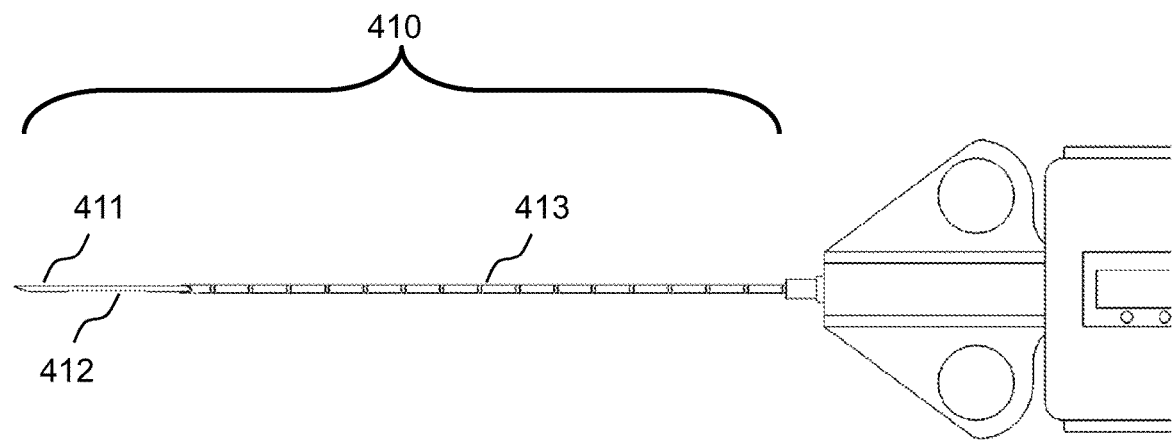
FIG. 8 shows a capturing tool of the testing device of FIG. 4 according to various embodiments.

To delineate the capture of the liver tissue sample during liver biopsy, the capture of the liver tissue sample is described in the following with reference to an embodiment of the industrial-standard core biopsy needle 410 portion of the "Lab-in-a-Needle" device 400 illustrated in FIG. 8. FIG. 8 shows a capturing tool 410 of the testing device 400 according to various embodiments. Specifically, the industrial-standard core biopsy needle may include an inner needle, stylet 411, and an outer needle, cutting cannula 413. The stylet 411 may contain a notch near the tip, specimen notch 412 (in other words a capturing element), to allow the collection of tissue in the stylet 411. The stylet 411 may protrude out by depressing the needle plunger 414 (FIG. 4) once the cutting cannula 413 advances to the region proximal to the tissue to be biopsied, and may capture tissue within the specimen notch 412 when needle plunger 414 is withdrawn. The surface of the stylet 411 may be coated with a non-stick layer (e.g. a form of polytetrafluoroethylene) to allow ease of tissue transfer from specimen notch 412 to the tissue transfer and lysis chamber 424 of the microfluidic chip 420. The cutting cannula 413 may serve for initial puncture and penetration to the site of biopsy. The cutting cannula 413 may be marked with 1 cm graduations to provide a means to indicate depth of penetration and may be visualized using conventional image-scanning equipment (MRI, ultrasound, X-ray) for compatibility with image-guided therapy. The typical length preferably ranges from 15 to 20 cm, with diameters preferably ranging from 14G to 18G.

FIG. 9 shows a capturing element 412 of the capturing tool 410 being withdrawn to position a tissue sample over a sample receiving port 424 of a microfluidic chip 420 according to various embodiments. Once the liver tissue sample has been captured by the stylet 411, the needle plunger 414 may be withdrawn to position the liver tissue sample over the tissue capture and lysis chamber 424. FIG. 9 shows the stylet 411 being withdrawn to position the liver tissue sample over the tissue capture and lysis chamber 424. An opening on the underside of the cutting cannula 413 may allow the passive transfer (via means of a non-stick coating) of the liver tissue sample from the specimen notch 412 into the tissue capture and lysis chamber 424. The needle plunger 414 may be depressed once again to close the opening to the tissue capture and lysis chamber 426. Once the liver tissue sample has been transferred ex-vivo to the microfluidic chip 420, the entire NAT process may proceed in the microfluidic chip 420.

Figure 10A:
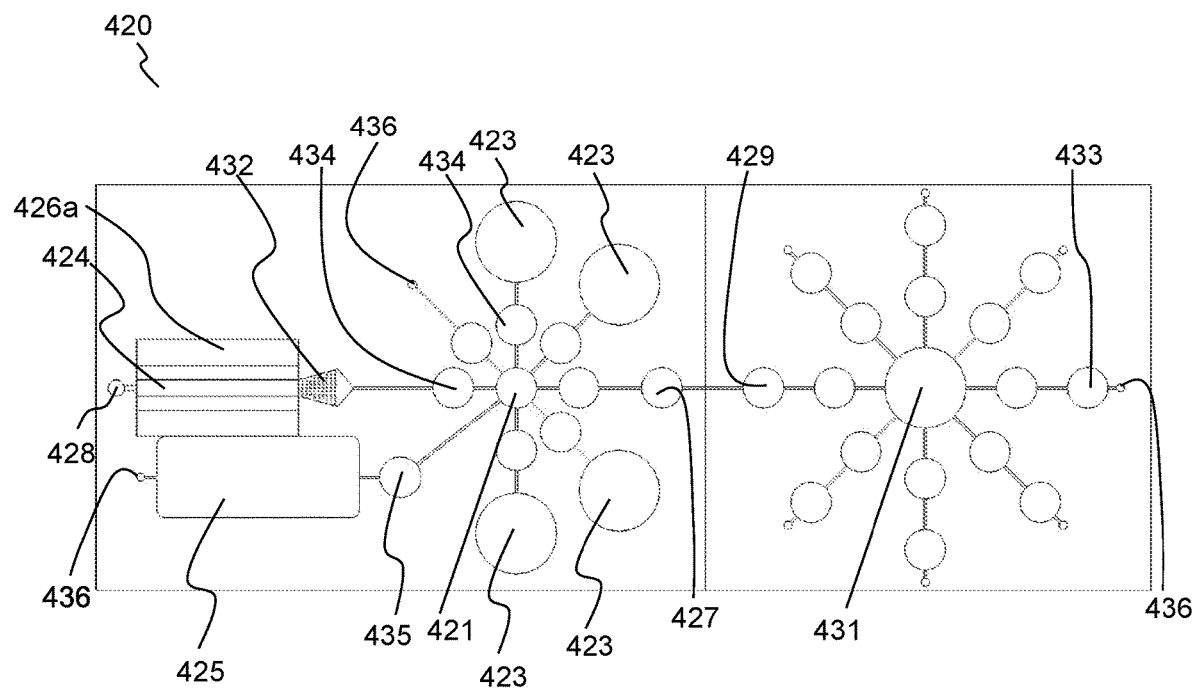
FIG. 10A shows a schematic drawing (plan-view) of a microfluidic chip of the testing device of FIG. 4 according to various embodiments.
Figure 10B:
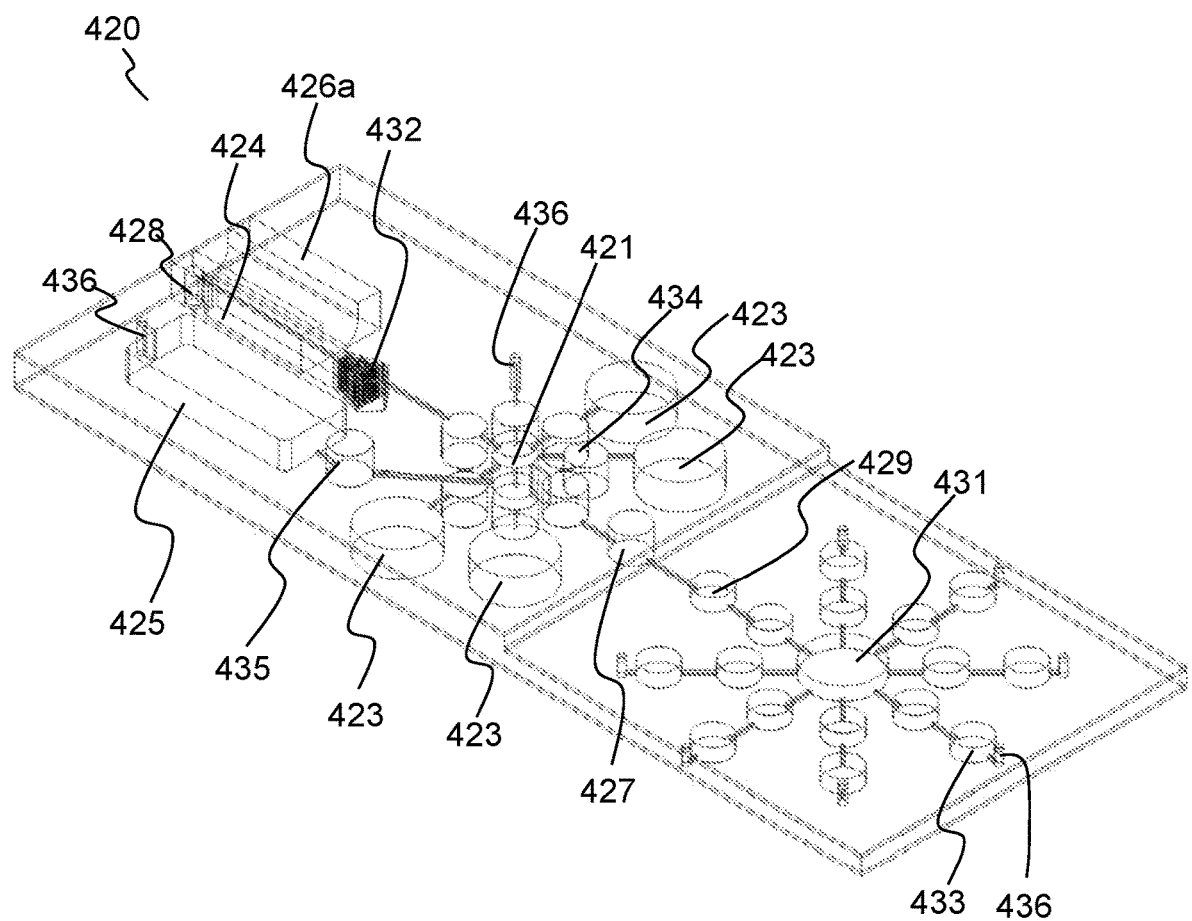
FIG. 10B shows an isometric view of the microfluidic chip of FIG. 10A according to various embodiments.

The polymeric microfluidic chip 420 may be an integral component of the aforementioned embodiment relating a POCT liver assessment device (or testing device) and may be a platform on which a method of using microfluidic NAT for liver assessment may takes place. FIG. 10A shows a schematic drawing (plan-view) of a microfluidic chip 420 according to various embodiments. FIG. 10B shows an isometric view of the microfluidic chip 420 according to various embodiments. To perform the complete NAT process comprising sample preparation, nucleic acid amplification and nucleic acid detection for liver assessment, the microfluidic chip 420 may include the following microfluidic structural components. As aforementioned, the sample actuation inlet 428 (in other words a sample actuation mechanism) may be connected to the electric air pump 474 via micro-tubing and may serve as the origin for sample/fluid actuation throughout the entire microfluidic chip 420.

As delineated earlier, once the sample, e.g. liver tissue, has been passively transferred from the specimen notch 412 of the stylet 411 into the tissue capture and lysis chamber 424, tissue and cellular lysis may be mechanically achieved via a vibrational shearing mechanism from a silica-sand coated piezoelectric disk embedded at the base of the microfluidic chip 420. Once the tissue sample has been sufficiently broken down, it may be actuated through filtration micro-pillars 432 (in other words a filter element) to a mRNA purification mixing chamber 421. The filtration micro-pillars 432 may be made from polycarbonate or poly(methyl methacrylate) using micro-milling, hot embossing or injection molding fabrication techniques. Functionally, these help to remove excessively large pieces of lysed tissues that remain after tissue lysis. The sample may pass through a one-way passive check valve 434 to prevent backflow from the mRNA purification mixing chamber 421.

The mRNA purification mixing chamber 421 may come preloaded with magnetic microbeads for mRNA extraction and purification and may contain a vibrational-based mixing function (preferably piezoelectric-based with flexible, deformable thin-film silica membranes) to sufficiently mix the lysis/washing/elution buffers from buffer reservoirs 423 with said microbeads for mRNA capture/hybridization. This mRNA extraction and purification method may be based on solid-phase extraction and the use of chaotropic buffers to allow the mRNA to bind to the microbeads. The mRNA purification mixing chamber 421 may lie in close proximity to an electromagnet built into the LOC frame 450 in order to allow the magnetic microbeads (with captured mRNA) to remain in the mixing chamber 421 as the lysis/washing buffers are being actuated into a waste reservoir 425.

Figure 11:
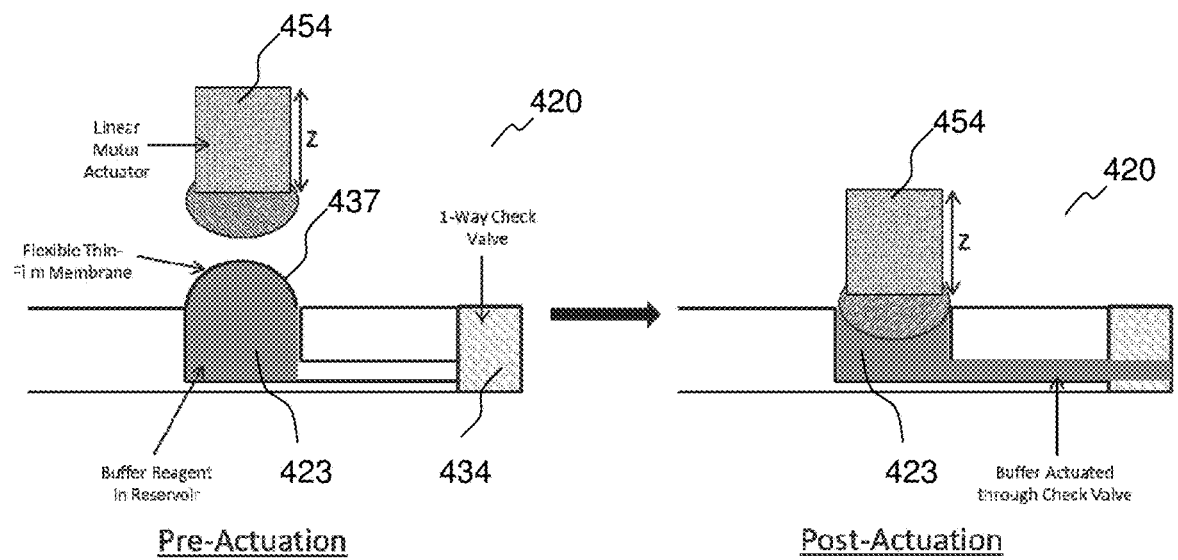
FIG. 11 shows a schematic diagram illustrating actuation of a buffer reservoir of the microfluidic chip of FIGS. 10A and 10B according to various embodiments.

The buffer reservoirs 423 may contain different preloaded buffer solutions necessary for mRNA extraction and purification. In one embodiment of said microfluidic chip 420, the mRNA extraction and purification protocol is based on the DYNABEADS® mRNA DIRECT™ Purification Kit (AMBION®, USA), which may include 4 different buffer solutions (Lysis/Binding buffer, Washing buffer A, Washing buffer B, Elution buffer). These buffers may be actuated into the mRNA purification mixing chamber 421 (through one-way passive check valves 434) via a specific sequential order as per manufacturer's protocol. Fluid actuation may be achieved via a plunger-actuated pump 454 (using linear motor actuators built into the LOC frame 450) on a flexible thin-film membrane 437 for compression deformation (see FIG. 11). FIG. 11 shows a schematic diagram illustrating actuation of the buffer reservoir 423 of the microfluidic chip 420 according to various embodiments.

The waste reservoir 425 may hold the used or excess lysis and washing buffers after they have been mixed with the microbeads in the mRNA purification mixing chamber 421. The fluid actuation force may be provided by the continued depression of linear motor actuators 454 in the buffer reservoirs 423, which pushes the buffers from the mRNA purification mixing chamber 421 (through the one-way active control valve 435) to the waste reservoir 425.

Once mRNA has been hybridized to the magnetic microbeads in the mRNA purification mixing chamber 421 and the unwanted tissue/cellular contaminants removed by the washing buffers, the elution buffer from the buffer reservoir 423 may be actuated into the mRNA purification mixing chamber 421, and into an elution chamber 427 with said microbeads. A microheater element on the LOC frame 450 may maintain a steady temperature of 70° C. for 2 minutes to allow the hybridized mRNA on the microbeads to be released into the solution. Subsequently, both the microbeads and the elution buffer (with the released mRNA) may be actuated into a microbeads capture chamber 429 that lies in close proximity to an electromagnet built into the LOC frame 450. The electromagnet may hold the magnetic microbeads (without any mRNA) in the microbeads capture chamber 429 as the purified mRNA sample in the elution buffer is transferred (through the one-way passive check valve 434) to a nucleic acid amplification mixing chamber 431.

The nucleic acid amplification mixing chamber 431 may come preloaded with nucleic acid amplification reagents, master mixes and fluorescence intercalating dye. The nucleic acid amplification mixing chamber 431 may embody a vibrational-based mixing function (preferably piezoelectric-based with flexible, deformable thin-film silica membrane) to sufficiently mix the purified mRNA sample transferred from the microbeads capture chamber 429 with the preloaded reagents. Once the reagents have been mixed with the purified mRNA sample, the nucleic acid assay may be actuated through one-way passive check valves 434 into multiple nucleic acid amplification reaction chambers 433 for reverse transcription of the mRNA into cDNA and the subsequent simultaneous amplification and detection of the cDNA. These nucleic acid amplification reaction chambers 433 may be preloaded with different sets of primers to allow for multiplex amplification of several target gene sequences simultaneously. The microheater element on the LOC frame 250 may allow thermal cycling to take place for nucleic acid amplification. Fluorescence detection by the camera module 478 may take place in these reaction chambers 433. The number of reaction chambers 433 may depend on the number of the target liver gene sequences.

The microfluidic chip 420 may also include vent outlets 436. The vent outlets 436 may aid in the specific flow and actuation of sample/fluid through the different components of the microfluidic chip 420.

Figure 12:
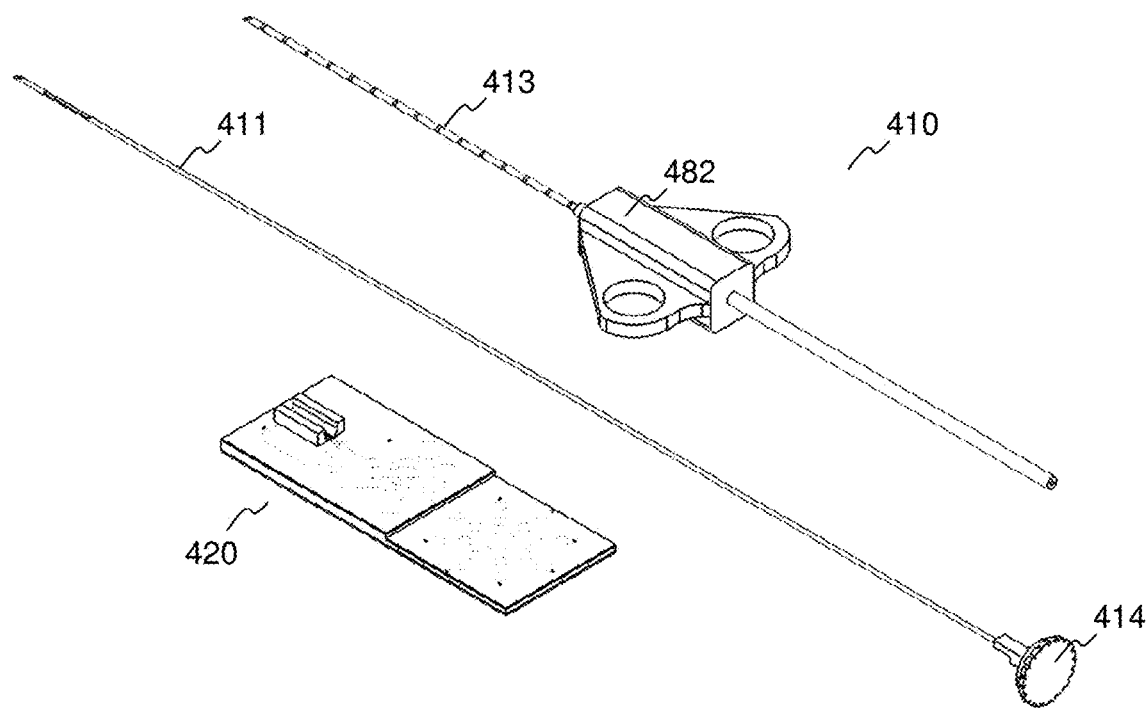
FIG. 12 shows the disposable components of the testing device of FIG. 4 according to various embodiments.

Congruous with the typical usage and disposability of industrial-standard core biopsy needles 410, the "Lab-in-a-Needle" diagnostic device 400 according to various embodiments may also include components which are envisioned to be detachable and disposable (see FIG. 12) so as to prevent cross-contamination between usages and to adhere to medically-accepted safety protocols. FIG. 12 shows the disposable components of the testing device 400 according to various embodiments. The parts that may be disposable may include the stylet 411 (attached to the needle plunger 414), the cutting cannula 413 (attached to the Handlegrip 482), as well as the polymeric microfluidic chip 420. The main components driving the LOC system may remain housed within the Mainbody 480 and may not be disposable so as to keep operating costs low.

Figure 13A:
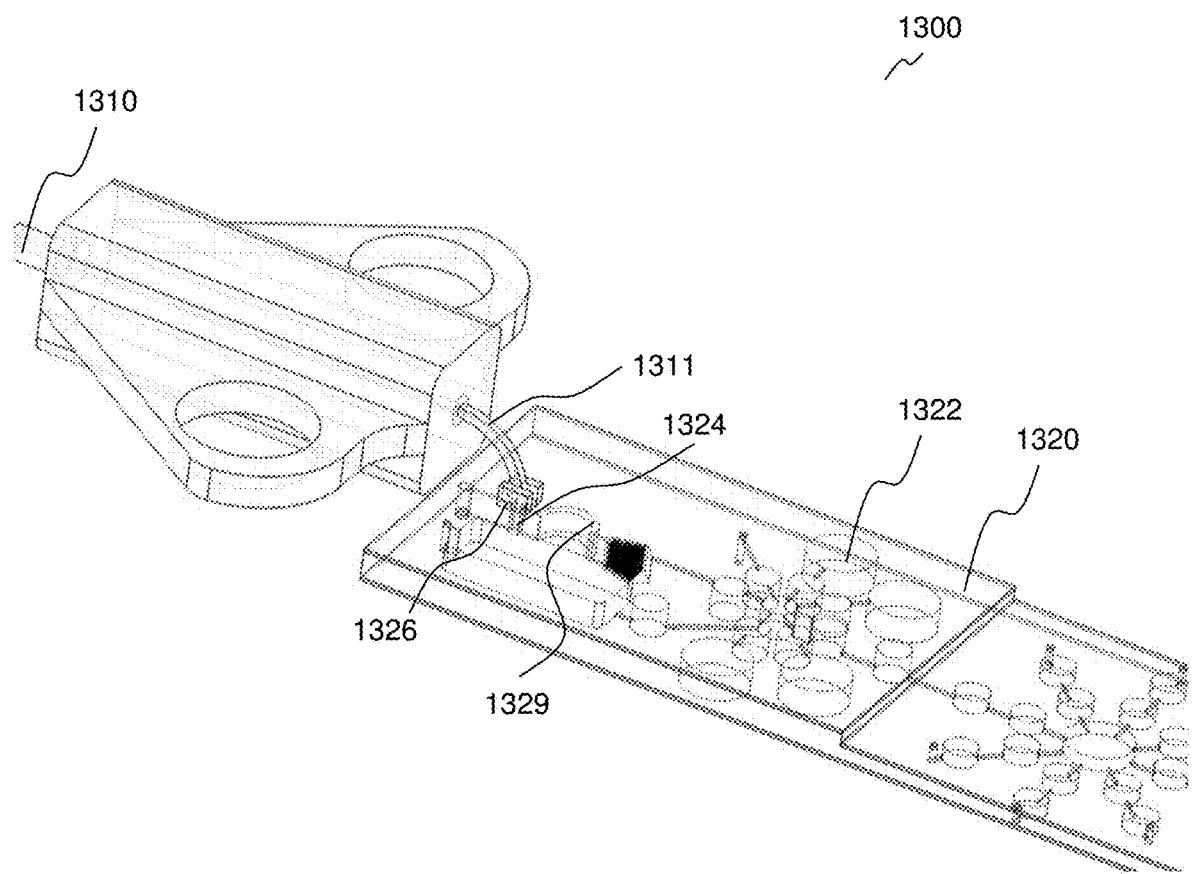
FIGS. 13A, 13B and 13C show a schematic drawing of the device for testing liquid sample according to various embodiments, and a perspective view and a side view of a portion of a microfluidic chip for receiving liquid sample according to various embodiments.

According to various embodiments, the "Lab-in-a-Needle" device and the microfluidic chip may be used for clinical analysis to body liquid sample such as blood, plasma, saliva, urine, etc. FIG. 13A shows a testing device 1300 ("Lab-in-a-Needle" device) for clinical analysis of body liquid according to various embodiments. As shown, the testing device may include a capturing tool 1310 and a microfluidic chip 1320. The capturing tool 1310 may include a needle, for example a hypodermic needle. The capturing tool 1310 may further include a biofluid transfer element 1311. The biofluid transfer element 1311 may include a tube, a conduit or the like. The microfluidic chip 1320 may include a plurality of chambers 1322 connected in a network. The microfluidic chip 1320 may include a sample receiving port 1324 connected to the network of the plurality of chambers 1322. The microfluidic chip 1320 may include a guide structure 1326 configured to receive the capturing tool 1310. The guide structure 1326 may include elevated sidewalls. As shown, the guide structure 1326 may be configured to receive the biofluid transfer element 1311 of the capturing tool 1310. Accordingly, the biofluid transfer element 1311 of the capturing tool 1310 and the guide structure 1326 may form a connection between the capturing tool 1310 and the microfluidic chip 1320. The guide structure 1326 may be configured to form a tight seal with the biofluid transfer element 1311, thus preventing leakage of fluid when fluid is transferred from the capturing tool 1310 to the microfluidic chip 1320 via the connection formed by the biofluid transfer element 1311 and the guide structure 1326. According to various embodiments, the capturing tool 1310 may be configured to capture sample in a distal position from the guide structure 1326 and further configured to transfer the captured sample to the sample receiving port in a proximal position from the guide structure 1326.

For example, in the scenario of using the testing device 1300 for arterial blood sampling. An end of the capturing tool 1310 proximal to the guide structure 1326 (in other words a proximal end of the needle) may be inserted into an artery of a patient. The arterial pressure would allow for passive transfer of blood into the capturing tool 1310 from the patient. At another end of the capturing tool 1310 distal to the guide structure, the blood in the capturing tool 1310 would then be transferred into the sample receiving port 1324 (in other words the transfer and lysis chamber) of the microfluidic chip 1320 via the biofluid transfer element 1311 and the guide structure 1326. The microfluidic chip 1320 may further include a one-way check valve before the sample receiving port 1324 such that flow of the blood sample into the sample receiving port 1324 may be controlled, for example only in one direction to prevent backflow.

Figure 13B:
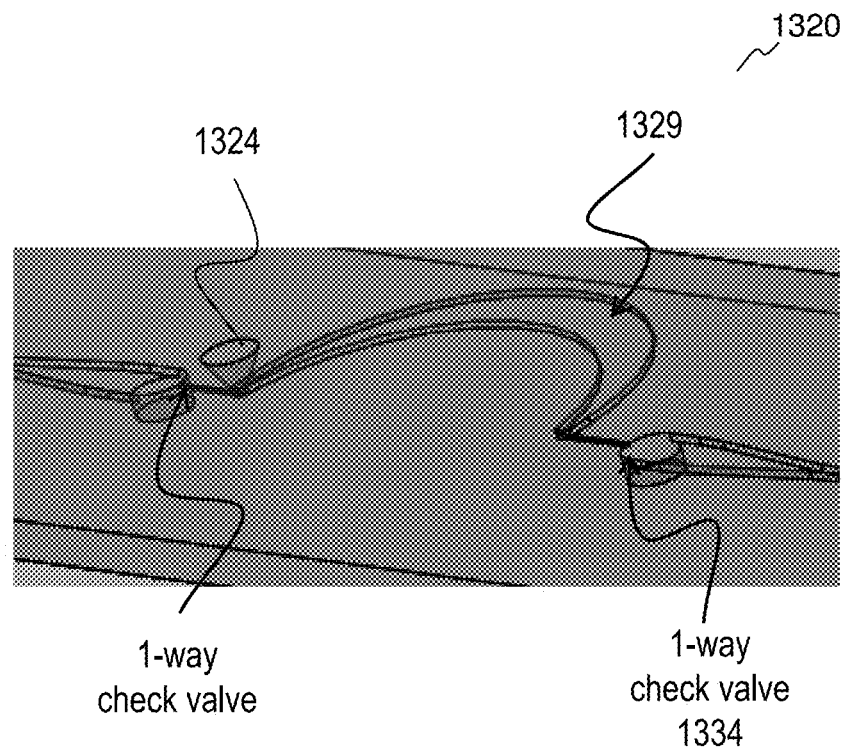
Figure 13C:
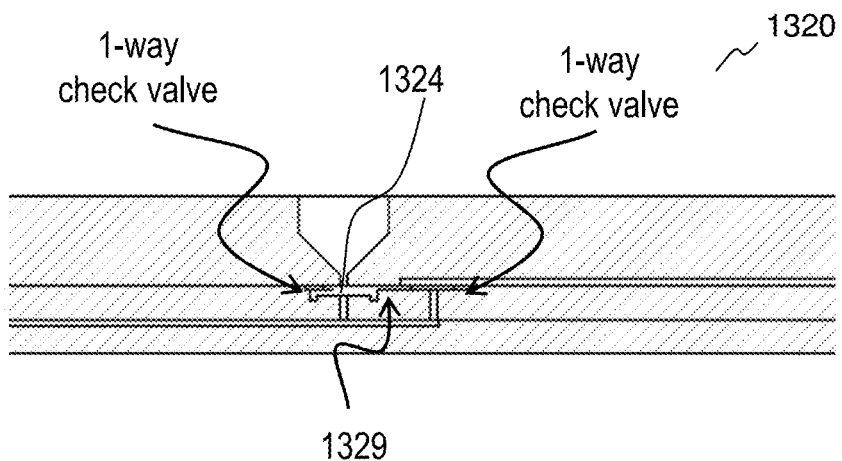

FIGS. 13B and 13C show a perspective view and a side view of a portion of the microfluidic chip 1320 for receiving liquid sample according to various embodiments. The liquid sample may be directly aspirated with desired volume, for example by the capturing tool 1310 of the testing device 1300, and loaded directly into sample receiving port 1324 of the microfluidic chip 1320. According to various embodiments, the microfluidic chip 1320 may include a metering channel 1329. The metering channel 1329 may be connected to the sample receiving port 1324. Liquid sample, for example blood sample, may flow into the metering channel 1329 via capillary force. The volume of loaded sample may be controlled by the volume of the metering channel 1329. The microfluidic chip 1320 may include one or more one-way check valve 1334. The microfluidic chip 1320 may include a one-way check valve 1334 between the sample receiving port 1324 and the metering channel 1329. The microfluidic chip 1320 may include a one-way check valve 1334 after the metering channel 1329, for example between the metering channel 1329 and the next chamber. The microfluidic chip 1320 may also include a one-way check valve 1334 before the sample receiving port 1324, for example between the guide structure 1326 and the sample receiving port 1324.

According to various embodiments, the other components of the testing device 1300 of FIG. 13A may be similar to the testing device 100, 101, 400 of FIGS. 1A, 1B, and 6-12. For example, similar to the testing device 100, 101, 400, the microfluidic chip 1320 of the testing device 1300 may include a sample actuation mechanism connected to an air pump for moving liquid sample throughout the microfluidic chip 1320.

According to various embodiments, the guide structure 1326 of the microfluidic chip 1320 of the testing device 1300 may be configured to allow direct loading of liquid sample into the sample receiving port 1324 of the microfluidic chip 1320 without using the capturing tool 1310 of the "Lab-in-a-Needle". For example, the guide structure 1326 may be configured to load liquid sample by using an external syringe.

According to various embodiments, there may be provided an integrated microfluidic NAT system (or a microfluidic chip) that may be applied to a practical POCT hepatotoxicity assessment device. The integrated microfluidic NAT system may embody both tissue sample preparation and multiplex real-time RT-PCR. The integrated microfluidic NAT system may include a first microfluidic chip for tissue sample preparation and a second microfluidic chip for multiplex real-time RT-PCR. The microfluidic system may feature semi-automation, may be relatively easy to use, and may have "sample-in-answer-out" capabilities for multiplex gene expression analysis. The tissue sample preparation module may incorporate both a microhomogenizer and surface-treated paramagnetic microbeads to perform on-chip tissue lysis and mRNA purification, allowing one to obtain high purity mRNA extracts, considerably better than manual means of extraction. A primer preloading surface treatment procedure and the single-loading assay inlet on a multiplex real-time RT-PCR module may simplify off-chip handling procedures, such as pre-mixing of different RT-PCR assays for multiple genes of interest (GOIs), for ease-of-use. Various embodiments may be advantageous in terms of being able to directly interrogate a crude liver tissue sample and investigate multiple gene targets in a single experimental run. Further, with an integrated fully quantitative methodology, various embodiments may be able to reduce the number of post-amplification procedural steps and diagnostic time, thereby allowing for the "sample-in-answer-out" diagnostic capability.

According to various embodiments, the microfluidic NAT system for a practical POCT hepatotoxicity assessment may embody three functions: tissue sample preparation, multiplex RT-PCR and real-time fluorescence detection for gene expression analysis.

Figure 14A:
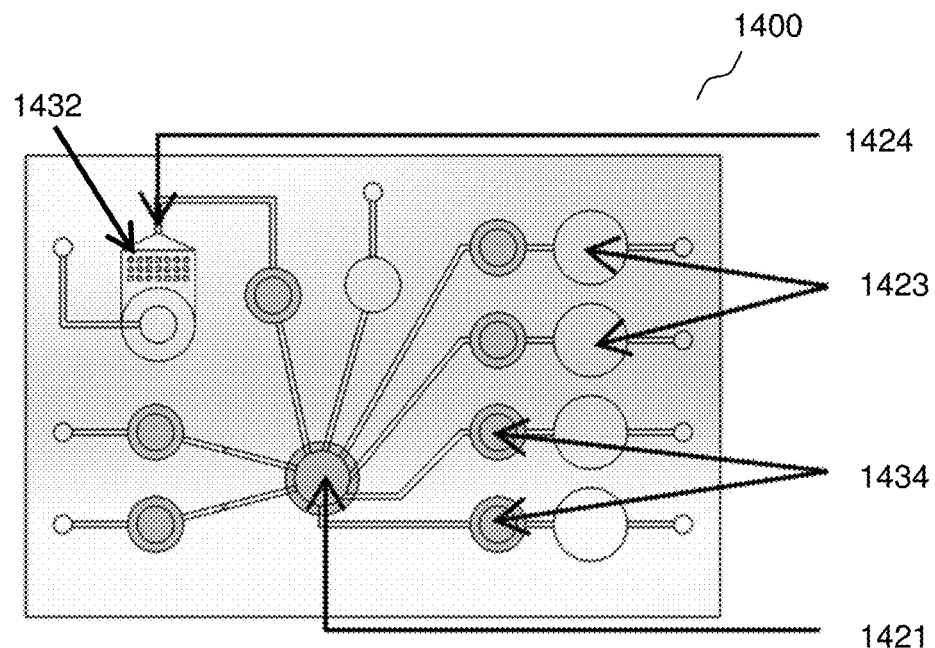
FIG. 14A and FIG. 14B show a microfluidic chip for sample preparing and mRNA extraction according to various embodiments.
Figure 14B:
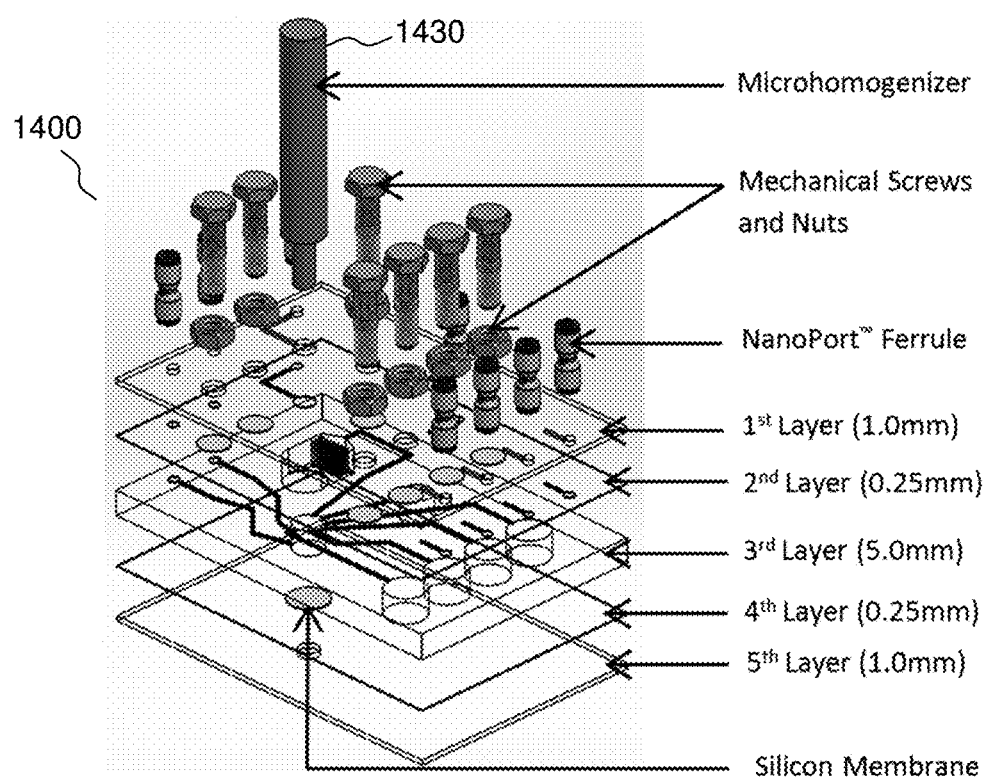

FIG. 14A and FIG. 14B show a first microfluidic chip 1400 for sample preparing and mRNA extraction according to various embodiments. The first microfluidic chip 1400 may be made of poly(methyl methacrylate) (PMMA). The first microfluidic chip 1400 (and the second RT-PCR microfluidic chip 1500 (FIG. 15A)) as shown was designed using SOLIDWORKS™ software and comprised five PMMA layers (FIG. 14B) patterned using $CO_2$ laser ablation with a 35W $CO_2$ laser (VERSALASER® VLS2.30, UNIVERSAL® Laser Systems, USA). Each PMMA layer may be subsequently cleaned in a bath sonicator with 10% v/v isopropanol for 15 minutes and dried in a vacuum oven at 80° C. overnight. All five layers may be clamped between two pieces of 5 mm thick borosilicate glass pieces and thermally bonded in an oven at 128° C. under 1 atm pressure for 2 h, followed by natural cooling to room temperature.

The first PMMA microfluidic chip 1400 may include four main components (see FIG. 14A) which may all be largely patterned in the $3^{rd}$ PMMA layer, including a tissue lysis chamber 1424, five reagent reservoirs 1423, a mixing chamber 1421 and seven mechanical valves 1434. The tissue lysis chamber 1424 may have a volume of ~250 µL, and worked in conjunction with a tissue microhomogenizer 1430 attachment (CLAREMONTBIO®, USA) which shredded and homogenized liver tissue samples placed within the chamber. Furthermore, an array of micro-pillars 1432 with dimensions of 500 µm×500 µm helped remove any unwanted tissue debris from the homogenized tissue lysate.

The first microfluidic chip 1400 may include four reagent reservoirs 1423 with volumes of 450 µL to preload and store buffers, and another 150 µL reagent reservoir for the paramagnetic microbeads from the DYNABEADS® mRNA DIRECT™ Purification Kit (AMBION®, USA). During the mRNA extraction process, these buffers and microbeads may be actuated from their respective reservoirs using external syringes.

For fluidic manipulation and control, mechanical valves 1434 may be incorporated into the first microfluidic chip 1400. The mechanical force exerted by the external screws (see FIG. 14B) may allow the flexible 0.25 mm thick silicon membrane (BISCO® Silicones, Rogers Corporation, USA, catalogue number HT-6240) to be directly deformed, thereby blocking microchannels and preventing solutions from passing through.

Lastly, the mixing chamber 1421 may have a volume of 150 µL, and may have the critical function of mixing the tissue lysate with the microbeads and relevant buffers for mRNA purification and extraction. This mixing function may be accomplished via an adopted aeroelasticity-based fluid agitation technique which used the spontaneous vibration of a silicone membrane (or diaphragm) induced by an external air flow.

Figure 15A:
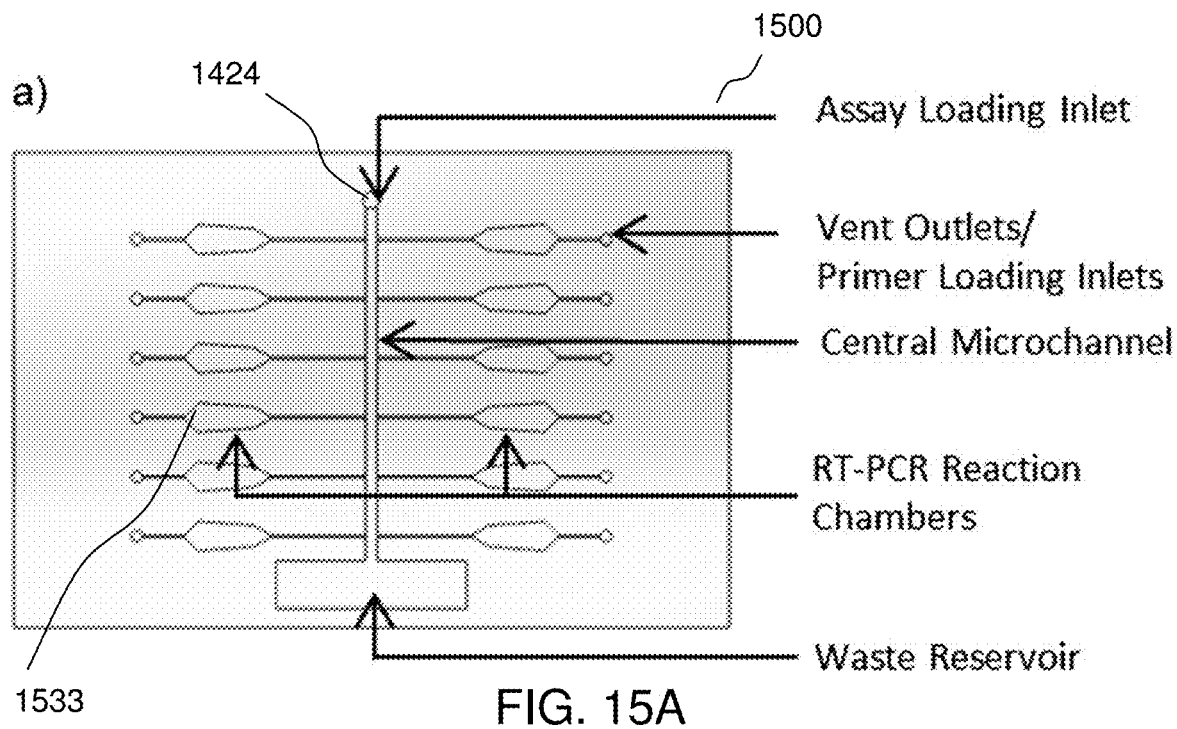
FIG. 15A and FIG. 15B show a microfluidic chip for multiplex real-time RT-PCR according to various embodiments.
Figure 15B:
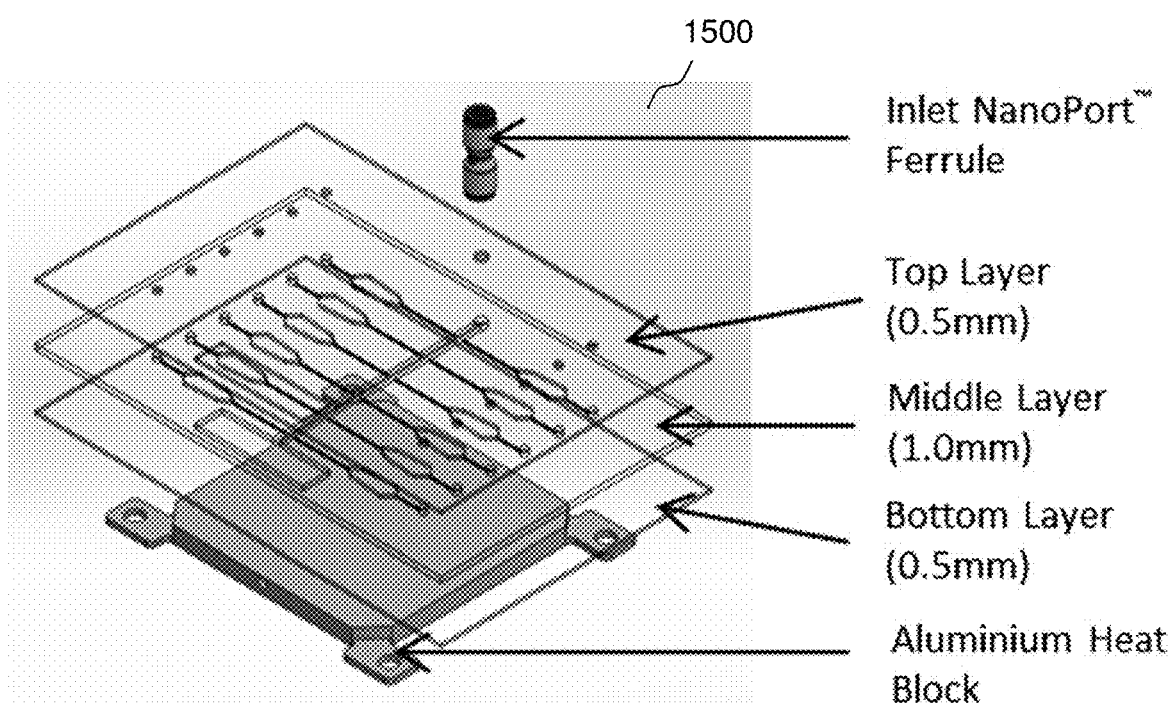

FIG. 15A and FIG. 15B show a second microfluidic chip 1500 for multiplex real-time RT-PCR according to various embodiments. The second microfluidic chip 1500 may include 12 reaction chambers 1533 connected to a central microchannel for multiplex RT-PCR reactions. Structurally, the RT-PCR reaction chambers 1533 may be cut into 1 mm thick middle layers, and their top and bottom surfaces may be enclosed by 0.5 mm thick PMMA top and bottom layers, respectively. This construction may ensure minimization of the surface roughness within the reaction chambers 1533 which may otherwise result in unwanted bubble formation during the PCR thermal cycling process.

The second microfluidic chip 1500 may include a single-assay loading inlet 1524 with attached NANOPORT™ PEEK ferrule connectors (UPCHURCH SCIENTIFIC®, USA) and 1/32" OD tubing. The RT-PCR assay may be derived from the upstream sample preparation microfluidic chip 1400 and may be actuated through this inlet 1524, and may be equally distributed into the 12 reaction chambers 1533. Each reaction chamber may have a volume of ~10 L, with microchannels of 5 mm by 0.2 mm to allow the RT-PCR assay to be loaded. To minimize the undesirable effect of evaporation and the formation of bubbles, a transparent adhesive PCR film seal (THERMO SCIENTIFIC®, Singapore) may be used to seal the vent outlets during the RT-PCR process.

According to various embodiments, also encompassed within the present invention is a method of using microfluidic Nucleic Acid Testing (NAT) for sample preparation, nucleic acid amplification, and nucleic acid detection. Accordingly, there is provided a method for determining a target messenger RNA (mRNA) in a tissue using the test device or microfluidic chip as disclosed herein, the method comprising the steps of (a) transferring a sample that has been obtained using a capture tool to a sample receiving port; (b) extracting RNA from the captured sample within the test device or microfluidic chip; and (c) determining the target mRNA by quantitative real-time reverse transcription polymerase chain reaction (real-time RT-PCR). Prior to step (c), the mRNA may be purified from the extracted RNA using the microbeads preloaded in the test device or microfluidic chip.

In preferred embodiments, step (c) may comprise the steps of (c1) reverse transcribing the mRNA into complementary DNA (cDNA); (c2) performing real-time RT-PCR; (c3) capturing fluorescence emissions using an image capturing mechanism at the annealing/extension phase of each cycle of real-time RT-PCR; (c4) calculating the cycle threshold (Ct) value for the real-time RT-PCR reaction based on the fluorescence emissions captured in step (d3); and (c5) determining the presence and/or amount of the target mRNA in the captured sample based on the calculated Ct value.

As set forth above, various elements and features of the test device and microfluidic chip of the invention are described in sufficient detail to fully enable the practice of the present method.

In sample preparation, the sample obtained from the capture tool is appropriately treated before it can be used in subsequent downstream applications. The sample is first lysed or broken down to release its cellular contents including the target mRNA biomarkers. This is followed by a filtration step to remove excess tissue or cellular debris to prevent microchannels blockage. Finally, the lysate is purified to remove the unwanted cellular contents and to allow the target mRNA biomarkers to be extracted.

Subsequently, the extracted and purified target mRNA biomarkers are first converted to cDNA, followed by PCR amplification to exponentially increase their concentration for detection purposes. Simultaneously, real-time fluorescence detection is used in conjunction with fluorescent DNA intercalating dye to detect and quantify the aforementioned exponential increase in cDNA concentration. This would allow real-time fluorescence graphs to be determined correlating fluorescence emission intensities to number of amplification cycles. From these graphs, the initial nucleic acid concentrations of the target mRNA biomarkers can be estimated via their respective average $C_t$ values (or cycle threshold); $C_t$ values are often used in quantitative PCR (or qPCR) as an indicator of starting/initial concentration of the nucleic acid template (Oblath, E. A., et al. *Lab Chip* 13, 1325-1332 (2013); Xiang, Q., et al. *Biomedical microdevices* 7, 273-279 (2005); Ramalingam, N. et al. *Sensors and Actuators, B: Chemical* 145, 543-552 (2010)).

Finally, once the initial nucleic acid concentrations of target mRNA biomarkers have been determined, analysis of up- or down-regulation of these mRNA biomarkers from the samples can be performed to ascertain, for example, the severity of liver damage and to complete a liver toxicity assessment.

As enabled by the test device or the microfluidic chip as disclosed herein, the method may be a multiplex method that allows simultaneous determination of a number of different target mRNAs.

In various embodiments, the present method may comprise determining at least one endogenous control mRNA, which may be a house-keeping gene selected from, without limitation, the group consisting of ACTB (β-actin), GAPDH (glyceraldehyde-3-phosphate dehydrogenase), RPLPO (ribosomal protein, large) and 18S (eukaryotic 18S ribosomal RNA). The selection and use of one or more endogenous control genes for the normalization of qPCR data, as routinely practiced, is within the knowledge of the skilled person.

In various embodiments, the present method may comprise using intron-spanning primers for specific detection of the target mRNA. Intron-spanning PCR primers refer to such primers which can only bind to a segment of the DNA which contains at least two adjacent exons, i.e. the interface of at least two exons. Such an intron-spanning PCR primer can, therefore, only bind under stringent conditions to intron-free DNA such as cDNA in a stable manner, but not to genomic DNA, since this is prevented by the intron sequences which are located between the exons on the genomic DNA, whereby ensuring that only the cDNA reverse transcribed from the target mRNA molecule is measured during the real-time RT-PCR.

The determined expression of one or more mRNA biomarkers may be used for the assessment of the tissue function, e.g. liver function. For liver function tests, one or more mRNAs selected from, without limitation, the group consisting of albumin (Alb), alanine transaminase (ALT), aspartate transaminase (AST), alkaline phosphatase (ALP), total bilirubin (TBIL), direct bilirubin (DBIL), and gamma glutamyl transpeptidase (GGT) may be determined using the method disclosed herein.

As will be understood by those skilled in the art, the assessment of liver function is usually not intended to be correct for 100% of the subjects to be diagnosed. However, the assessment may be correct for a statistically significant portion of the subjects (e.g. a cohort in a cohort study). Thus, the method of the present invention at least provides an aid for establishing a final clinical diagnosis.

Various embodiments as described herein may have addressed the underlying key issues with the prior-art gold standards of disease assessment in terms of being logistically complicated, labour-intensive, time consuming and largely incompatible with POCT for personalized or precision medicine. According to various embodiments, there is provided an instrument capable of a simplified and medically-acceptable procedure for disease diagnosis, and a method of using microfluidic NAT, including for liver assessment. Various embodiments have also provided an easy-to-use POCT diagnostic device with "sample-in-answer-out" capabilities, including for liver assessment.

Advantageously, the various embodiments of the testing device (or the lab-in-the-needle) differentiates from conventional microfluidic chips or detection systems in that the former is completely in vivo and conducted in an enclosure (needle, chip etc) and does not involve expose to ex vivo environment and multiple transfers involving several external processing machines as the current microfluidic chips.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

EXAMPLES

Materials and Methods
A. Biological Samples

A short-term (5 days) preclinical drug toxicity experiment was performed on common black laboratory mice (Strain name: C57BL/6J; Age: 5-7 weeks). All experiments were performed in accordance with the National Institutes of Health Guide for the care and use of laboratory animals (NIH Publications No. 80-23, revised 1996) and conducted after approval by the Institutional Animal Care and Use Committee of Houston Methodist Research Institute (HMRI).

A total of eight mice were divided into two equal groups, with one mouse in each group designated as the control and the remaining three subjected to drug treatment. The drug used was cyclophosphamide (200 mg/kg body wt.) (E. Anton, *British journal of experimental pathology*, 1987, 68, 237-249), and the control used was saline with concentration of 0.9% w/v NaCl. The drug was administered through intraperitoneal route, with the first group having a single dose administered on the $1^{st}$ day only; and the second group having 3 doses administered on the $1^{st}$, $3^{rd}$ and $5^{th}$ days. The animals were subsequently euthanized following standard carbon dioxide anaesthesia procedure on the $5^{th}$ day after final drug administration. The mouse liver tissues were thereafter silated, and cut into equal small pieces (~20-30 mg) and stored in RNAlater RNA Stabilization Reagent (QIAGEN®, USA) at 4° C. to prevent RNA degradation.

B. Sample Reparation and mRNA Extraction Chip Design and Fabrication

The poly(methyl methacrylate) (PMMA) microfluidic chip disclosed herein for the sample preparation and mRNA extraction is depicted in FIG. 14A. The microfluidic chip (and subsequent RT-PCR microfluidic chip) was designed using SOLIDWORKS™ software and comprised five PMMA layers (FIG. 14B) patterned using $CO_2$ laser ablation with a 35W $CO_2$ laser (VERSALASER® VLS2.30, UNIVERSAL® Laser Systems, USA). Each PMMA layer was subsequently cleaned in a bath sonicator with 10% v/v isopropanol for 15 minutes and dried in a vacuum oven at 80° C. overnight. All five layers were clamped between two pieces of 5 mm thick borosilicate glass pieces and thermally bonded in an oven at 128° C. under a 1 atm pressure for 2 hrs, followed by natural cooling to room temperature.

The PMMA chip comprised four main components (see FIG. 14A) which were all largely patterned in the $3^{rd}$ PMMA layer, including a tissue lysis chamber, five reagent reservoirs, a mixing chamber, and seven mechanical valves. The tissue lysis chamber had a volume of ~250 µL, and worked in conjunction with a tissue microhomogenizer attachment (CLAREMONTBIO®, USA) which shredded and homogenized liver tissue samples placed within the chamber. Furthermore, an array of micropillars with dimensions 500 µm×500 µm helped to remove any unwanted tissue debris from homogenized tissue lysate.

The chip design disclosed herein included four reagent reservoirs with volumes of 450 µL to preload and store buffers, and another 150 µL reagent reservoir for the paramagnetic microbeads from the DYNABEADS® mRNA DIRECT™ Purification Kit (AMBION®, USA). During the mRNA extraction process, these buffers and microbeads were actuated from their respective reservoirs using external syringes.

For fluidic manipulation and control, mechanical valves were incorporated into the microfluidic chip. The mechanical force exerted by the external screws (see FIG. 14B) allowed the flexible 0.25 mm thick silicon membrane (BISCO® Silicones, Rogers Corporation, USA, catalogue number HT-6240) to be directly deformed, thereby blocking microchannels and preventing solutions from passing through (R. Mohan, et al, *Sensors and Actuators B: Chemical*, 2011, 160, 1216-1223).

Lastly, the mixing chamber had a volume of 150 µL, and had the critical function of mixing the tissue lysate with the microbeads and relevant buffers for mRNA purification and extraction. This mixing function was accomplished via an adopted aeroelasticity-based fluid agitation technique (H. M. Xia, et al. *Lab Chip*, 2012, 12, 60-64; H. M. Xia, et al. *Lab on a Chip*, 2013, 13, 1619-1625) which used the spontaneous vibration of a silicone membrane (or diaphragm) induced by an external air flow.

C. Multiplex RT-PCR Chip Design and Fabrication

The proposed PMMA chip consisted of 12 reaction chambers connected to a central microchannel for multiplex RT-PCR reactions. Structurally, the RT-PCR reaction chambers were cut into the 1 mm thick middle layer, and their top and bottom surfaces were enclosed respectively by 0.5 mm thick PMMA top and bottom layers. This construction ensured minimization of the surface roughness within the reaction chambers which would otherwise result in unwanted bubble formation during the PCR thermal cycling process (H. B. Liu, et al. *Journal of Micromechanics and Microengineering*, 2007, 17, 2055-2064).

The chip design disclosed herein comprised a single assay loading inlet with attached NANOPORT™ PEEK ferrule connectors (UPCHURCH SCIENTIFIC®, USA) and 1/32" OD tubing. The RT-PCR assay derived from the upstream sample preparation microfluidic chip was actuated through this inlet, and was equally distributed into the 12 reaction chambers. Each reaction chamber had a volume of ~10 µL, with microchannels of 5 mm by 0.2 mm to allow the RT-PCR assay to be loaded. To minimize the undesirable effect of evaporation and the formation of bubbles, transparent adhesive PCR film seal (THERMOSCIENTIFIC®, Singapore) was used to seal the vent outlets during the RT-PCR process.

D. Liver Tissue Sample Preparation and mRNA Extraction on Microfluidic Chip

Figure 16:
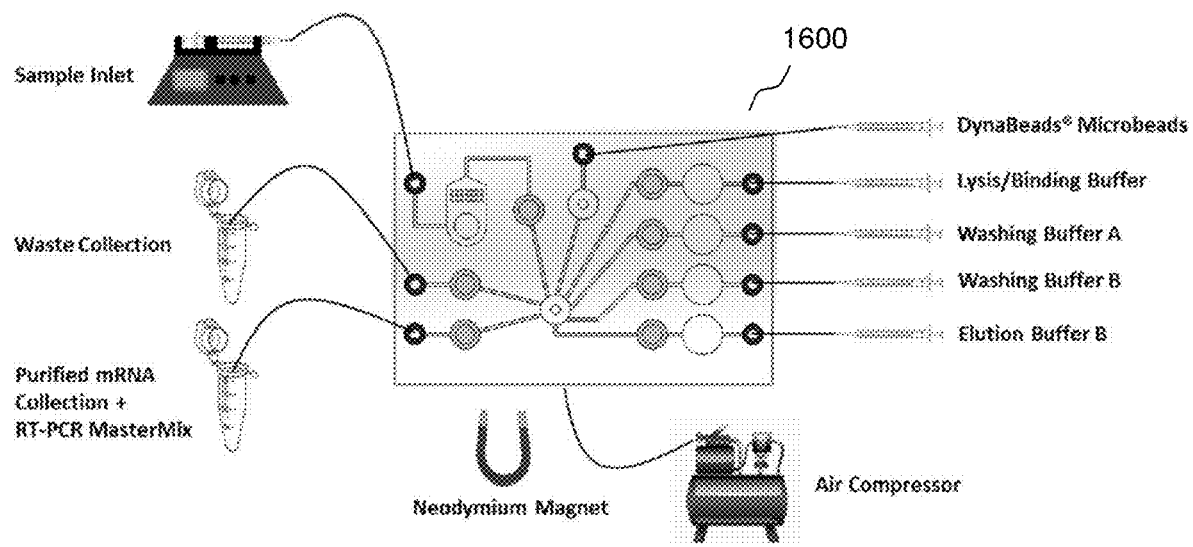
FIG. 16 shows a schematic diagram illustrating the tissue sample preparation setup featuring a syringe pump, PMMA microfluidic chip with preloaded microbeads and buffers in reagent reservoir chambers, external EPPENDORF® tubes for collection, and an external air compressor to provide a chamber mixing function.

For this procedure, all instruments, microfluidic chips and equipment used were first sterilized with the ULTRACLEAN® Lab Cleaner (MO-BIO LABORATORIES®, USA) and the experiment performed in a biosafety level 2 cabinet to minimize the presence of RNases. To prepare the microfluidic chip for sample preparation, 150 µL of DYNABEADS® microbeads solution stored in the reagent reservoir was actuated into the mixing chamber using a 250 µL HAMILTON® glass syringe (SIGMA-ALDRICH®, Singapore, catalogue number 24538-U), and a programmable syringe pump (NEW ERA PUMP SYSTEMS® Inc., USA, model number NE-1002x) at a flow rate of 100 µL/min (see FIG. 16—schematic diagram 1600 illustrating the tissue sample preparation setup, DYNABEADS® microbeads).

450 µL Lysis/Binding buffer stored in another reagent reservoir on the chip was actuated into the mixing chamber to pre-condition the microbeads for subsequent mRNA binding. The mixing function was provided by the aeroelastic vibrational action of a thin-film silica diaphragm caused by the external air compressor (H. M. Xia, et al. *Lab Chip,* 2012, 12, 60-64; H. M. Xia, et al. *Lab on a Chip,* 2013, 13, 1619-1625). Once the paramagnetic microbeads were pre-conditioned, the excess Lysis/Binding buffer was actuated into the Waste Collection EPPENDORF® tube whilst the microbeads were held within the mixing chamber with external neodymium magnets.

A liver tissue sample, weighing approximately 20-30 mg, was loaded directly into the tissue lysis chamber. The tissue sample was secured within the chamber when the tissue microhomogenizer attachment was fitted into the opening of the lysis chamber. Subsequently, 250 µL Lysis/Binding buffer was loaded into another 250 µL glass syringe (see FIG. 16, Sample Inlet), and actuated into the tissue lysis chamber at a flow rate of 200 µL/min. For tissue lysis, the microhomogenizer attachment was activated for ~1 min to allow the liver tissue to be shredded and homogenized. After the completion of tissue lysis, the unwanted tissue debris and supernatant were removed by the micro-pillars as the homogenized tissue lysate was actuated into the mixing chamber, where the lysate was mixed with the microbeads for ~8 mins to allow for mRNA binding.

The subsequent mRNA extraction and purification steps were performed using 450 µL Washing buffers A/B as per a modified version of the manufacturer's suggested protocol, with a final extraction volume of 30 µL (using the Elution buffer). The purified mRNA from each mouse liver tissue sample was collected in an EPPENDORF® tube preloaded with an RT-PCR master mix. To validate the efficacy of our sample preparation microfluidic chip, purified mRNA solutions extracted using our microfluidic chip was tested for their purity using the NANODROP™ 2000 (THERMOSCIENTIFIC®, Singapore), to ensure an A260/280 ratio of ~2.0-2.2 before proceeding to the subsequent downstream applications of RT-PCR and nucleic acid detection.

E. Preloading of PCR Primers on Microfluidic Chip

Both forward and reverse primers of the two GOIs (AST and ALT) and the housekeeping gene f-actin were preloaded through the vent outlets/primer loading inlets (FIG. 14A) after the PMMA microfluidic chip had been thermally bonded and sterilized under ultraviolet (UV) radiation for 15 minutes. 50 µM of each primer (forward and reverse) was diluted in nuclease-free water to make up a final-volume of 10 µL and final-primer concentration of 0.5 µM. The preloading process was performed using a micropipette, and the 12 chambers were separated into three groups to be treated with the AST, ALT and β-actin primer pairs respectively.

Subsequently, the preloaded chip was dried in a convection oven at 65° C. for 15 minutes to allow the water in the primer solution to evaporate, leaving the dried primers deposited as powder form in the individual reaction chambers. This surface treatment process would allow simultaneous amplification of multiple GOIs with a single RT-PCR assay.

F. Multiplex RT-PCR on Microfluidic Chip

Once the purified mRNA had been extracted from the liver tissue samples, 30 µL of the purified mRNA extract (i.e. elution buffer with the microbeads) was collected in an EPPENDORF® tube containing the following RT-PCR composition: 75 µL 2× SYBR Green RT-PCR reaction mix (BIORAD®, Singapore), 3.0 µL iSCRIPT™ One-Step RT-PCR reverse transcriptase (BIORAD®, Singapore) and 42 µL nuclease-free water. This 150 µL final RT-PCR assay was subsequently transferred from the EPPENDORF® tube into a 250 µL HAMILTON® glass syringe connected to the RT-PCR microfluidic chip via a 1/32" OD tubing.

Figure 17:
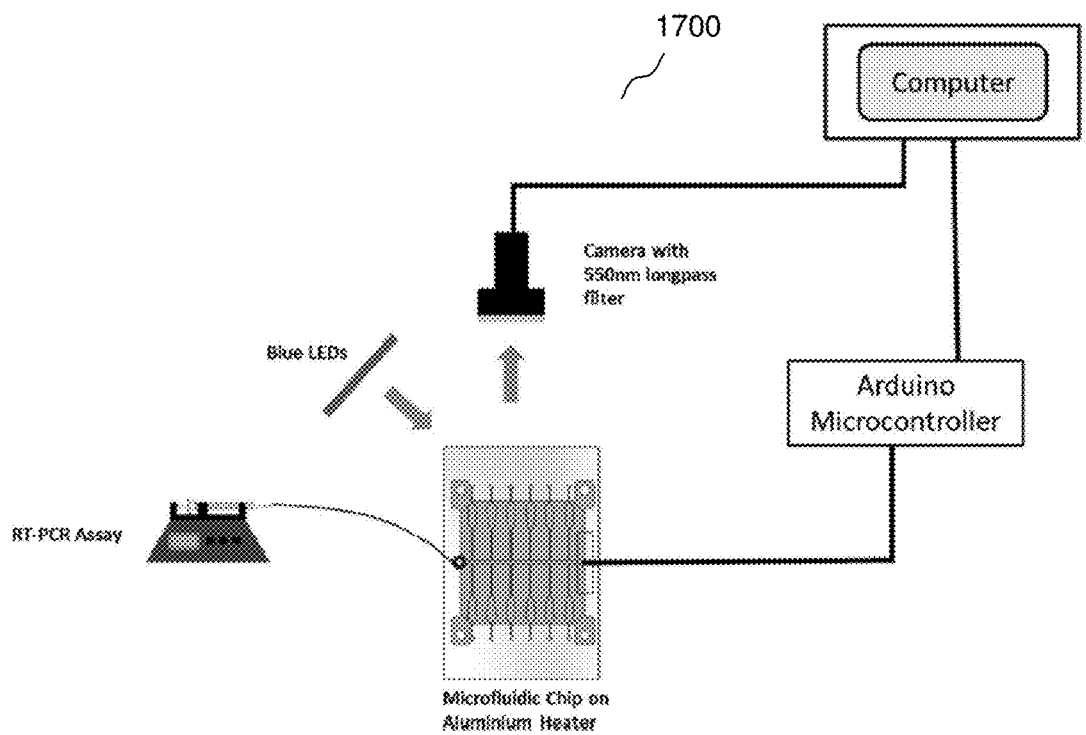
FIG. 17 shows a schematic diagram illustrating the multiplex microfluidic real-time RT-PCR setup featuring a syringe pump, PMMA microfluidic chip on an aluminum heater connected to an ARDUINO® microcontroller, and 3MP CMOS camera module with 550 nm longpass filter and 470 nm blue excitation LEDs connected to a computer.

To demonstrate the functionality of the multiplex RT-PCR microfluidic chip, the purified mRNA extracted from the mouse liver tissue samples was subjected to thermal cycling on a chip-compatible aluminium block thermal cycler. The chip-compatible thermal cycler was based on the open-source OpenPCR® (Chai Biotechnologies, USA) platform, using a custom-designed aluminium metal block for contact-based thermal cycling and an ARDUINO® microcontroller for precise temperature control (see FIG. 17—schematic diagram 1700 illustrating the multiplex microfluidic real-time RT-PCR setup).

For multiplex gene expression analysis, two different GOIs (i.e. AST and ALT) were amplified concurrently in each experimental run. The subsequent final cDNA concentrations of said GOIs were compared between the animals with and without drug treatment for gene expression analysis. Intron spanning primers were used for our two GOIs to ensure specific amplification of the transcribed mRNA and not the genomic DNA (see Table 1). These AST and ALT primers were designed using the PRIMERQUEST® software (INTEGRATED DNA TECHNOLOGIES®, Singapore) and synthesized de novo, from the same company. For the housekeeping gene, β-actin was selected and used in the quantitative PCR (qPCR) experiments for normalization of data. β-actin is a common housekeeping gene that is widely used as a positive control in qPCR of mouse tissues due to its constitutive expression (K. E. Kouadjo, et al. *BMC Genomics,* 2007, 8, 127; E. d. L. Rebouças, et al. *Brazilian Archives of Biology and Technology,* 2013, 56, 143-154). The β-actin primer assay was obtained from QIAGEN®, Singapore (Catalog No. PPM02945B), with a band size of 154 bp.

TABLE 1

RT-PCR targets and primers sequences (5'-3').

| SEQ ID NO | Sequence name | Nucleic acid sequence | Number of base pairs |
|---|---|---|---|
| 1 | AST (Target) | GCT GAC TTC TTA GGG CGA TGG<br>TAC AAT GGT ACA GAT AAC<br>AAG AAC ACA CCA ATC TAC<br>GTA TCA TCA CCA ACC TGG GAG<br>AAC CAT AAT GCT GTG TTT TCT<br>GCC GCC GGT TTT AAG GAC ATT<br>CGG CCC TAT TGC TAC TGG GAT<br>GCG GAG AAG AGA GGA CTG | 182 |

TABLE 1-continued

RT-PCR targets and primers sequences (5'-3').

| SEQ ID NO | Sequence name | Nucleic acid sequence | Number of base pairs |
|---|---|---|---|
|  |  | GAC CTC CAG GGT TTC CTG AAT GA |  |
| 2 | AST Forward Primer | GCT GAC TTC TTA GGG CGA TG |  |
| 3 | AST Reverse Primer | TCA TTC AGG AAA CCC TGG AG |  |
| 4 | ALT (Target) | CTG CAG ACC CGA ACA ACA TAT TTC TGT CCA CAG GGG CCA GCG ATG CCA TCG TGA CCA TGC TCA AGC TGC TGG TAG CCG GCG AGG GCC GTG CGC GAA CCG GTG TAC TCA TTC CCA TTC CTC AGT ACC CAC TGT ACT CAG CTG CGC TGG CTG AGC TGG ACG CCG TGC AAG TGG ACT ACT ACC TGA ACG AAG AGC GCG CCT GGG CTC TTG ACA TCG CTG AGC TG | 221 |
| 5 | ALT Forward Primer | CTG CAG ACC CGA ACA ACA TA |  |
| 6 | ALT Reverse Primer | CAG CTC AGC GAT GTC AAG AG |  |
| 7 | β-Actin (Housekeeping Gene) | GGC TGT ATT CCC CTC CAT CGT GGG CCG CCC TAG GCA CCA GGG TGT GAT GGT GGG AAT GGG TCA GAA GGA CTC CTA TGT GGG TGA CGA GGC CCA GAG CAA GAG AGG TAT CCT GAC CCT GAA GTA CCC CAT TGA ACA TGG CAT TGT TAC CAA CTG G | 154 |
| 8 | β-Actin Forward Primer | GGC TGT ATT CCC CTC CAT CG |  |
| 9 | β-Actin Reverse Primer | CCA GTT GGT AAC AAT GCC ATG T |  |

Figure 18:
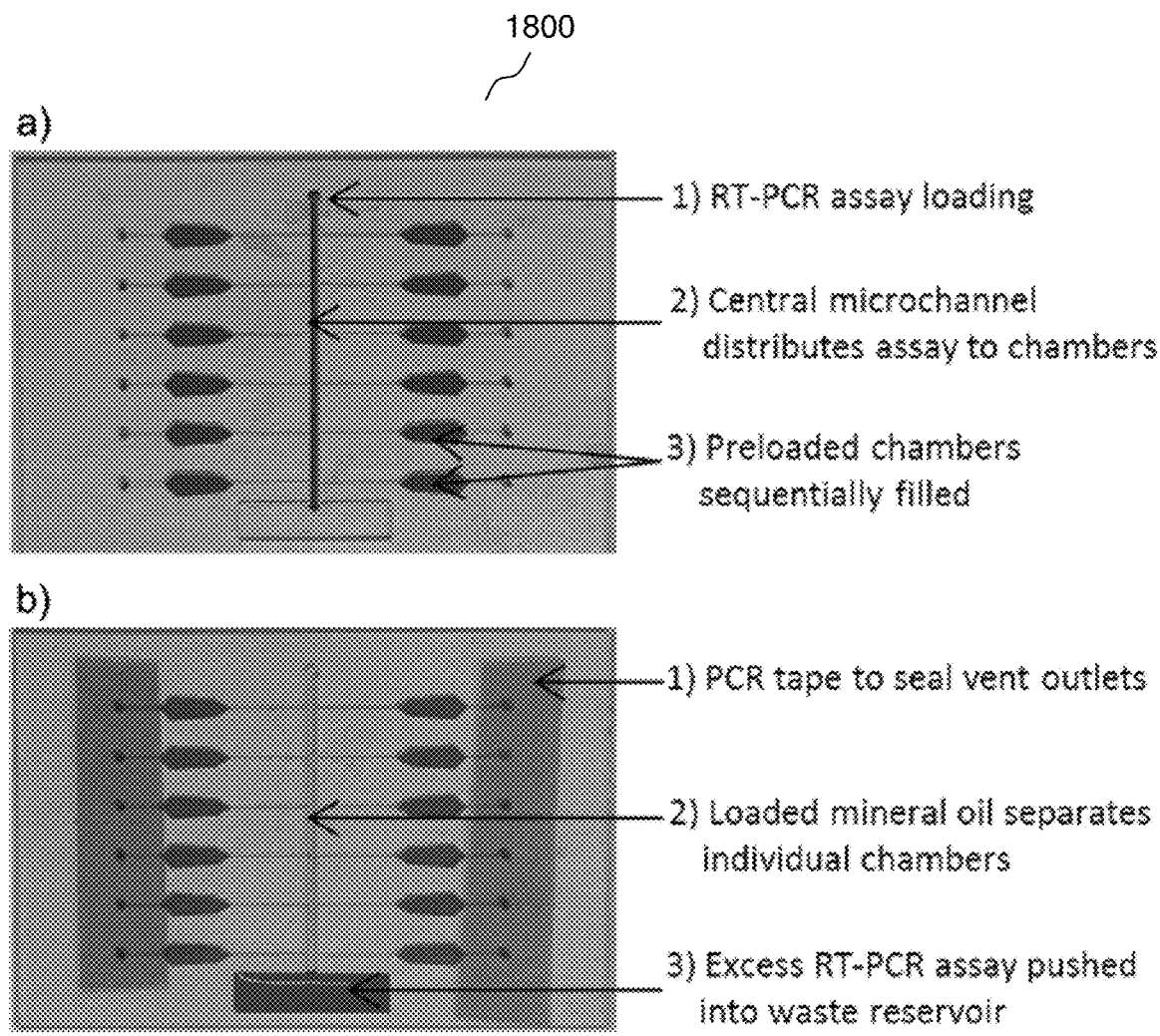
FIG. 18 shows an illustration of RT-PCR microfluidic chip preparation with colored dye and brown adhesive tape: a) Loading of RT-PCR assay into single loading inlet to be sequentially distributed into preloaded reaction chambers; b) Sealing of vent outlets and loading of immiscible mineral oil to separate individual reaction chambers to prevent cross-contamination.

To prepare the microfluidic chip for multiplex RT-PCR, the RT-PCR assay was actuated into the 12 reaction chambers using a programmable syringe pump at a flow rate of 50 μL/min. Once all 12 reaction chambers were sequentially filled with the RT-PCR assay, their vent outlets were sealed with the aforementioned transparent adhesive PCR film seal. Subsequently, 30 μL of an immiscible PCR-grade mineral oil (SIGMA-ALDRICH®, Singapore) was actuated using the syringe pump to remove the excess RT-PCR assay remaining in the central microchannel (into the waste reservoir). The separation of the RT-PCR assays in individual reaction chambers by the immiscible mineral oil prevents any cross-contamination during the thermal cycling process. The sequence of events illustrating the microfluidic chip preparation process 1800 is depicted in FIG. 18.

To provide a benchmark reference to the chip disclosed herein, the same RT-PCR assays (with addition of forward/reverse primers at 0.5 μM concentration) were amplified separately in EPPENDORF® tubes on a conventional CFX96 TOUCH™ Real-Time PCR Detection System (BIO-RAD®, USA).

The thermal cycling process was as follows: 70° C. for 2 mins to allow dehybridization of the captured mRNA from the microbeads, followed by 50° C. for 10 minutes for reverse transcription, subsequently with an initial denaturation step of 95° C. for 5 mins and finally 35 cycles of PCR, comprising two stages: denaturation at 95° C. for 10 s and annealing/extension at 55° C. for 30 s.

G. Fluorescent Detection of Amplified cDNA

Figure 19:
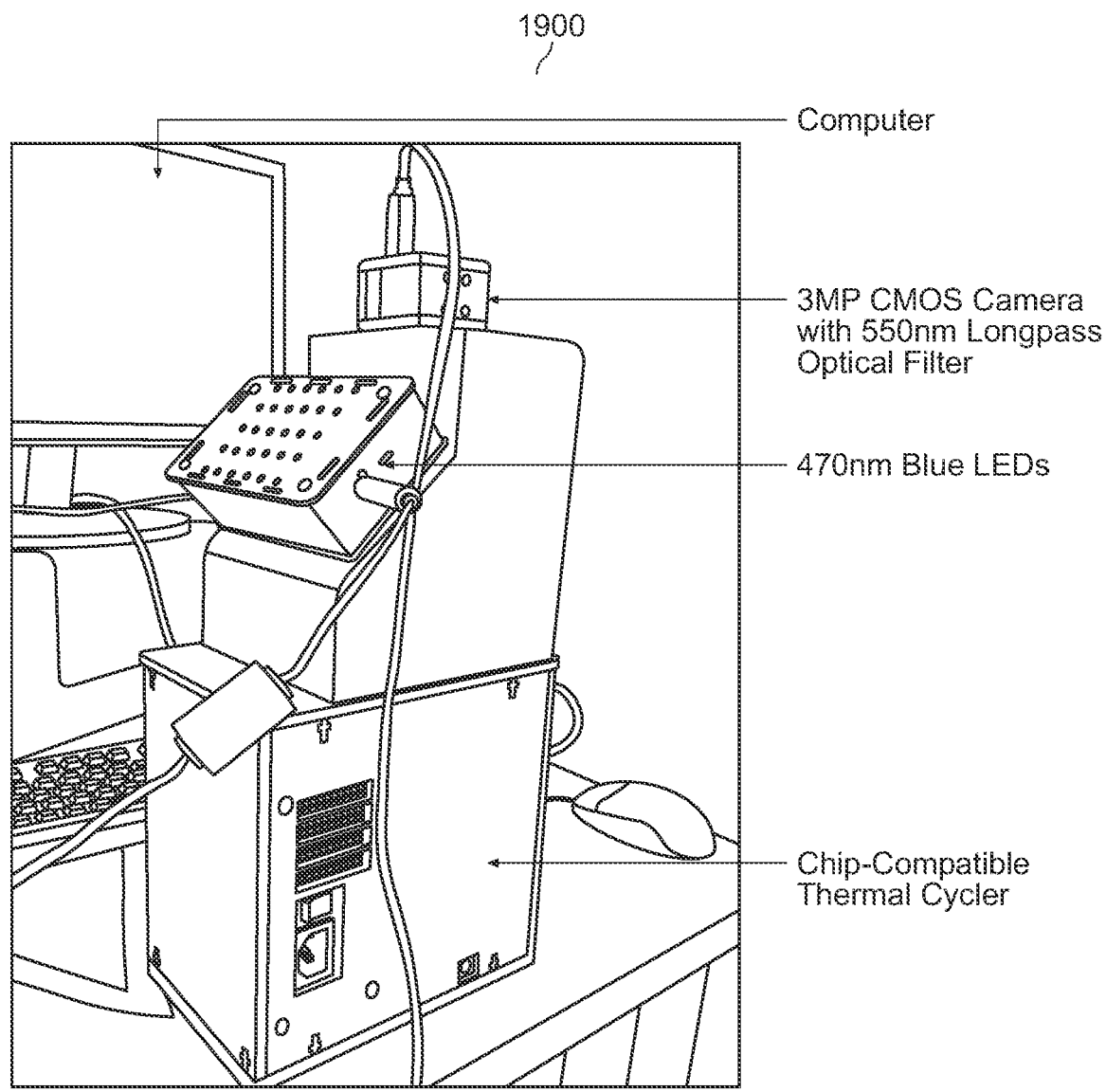
FIG. 19 shows the RT-PCR and fluorescent detection setup: Photograph of entire microfluidic setup with a chip-compatible thermal cycler and attached fluorescent detection module.

To enable simultaneous fluorescent detection of amplified cDNA for a fully-quantitative methodology, the inventors developed an image capturing system embodying a camera module with blue excitation LEDs to be mounted on the chip-compatible thermal cycler disclosed herein (FIG. 19—RT-PCR and fluorescent detection setup 1900). A 3MP CMOS camera with mounted 550 nm longpass optical filter (ISLAND OPTICAL SYSTEMS®, Singapore) was fitted onto a black opaque acrylic frame with a 470 nm blue LED module (IORODEO®, USA) to provide an excitation source for the SYBR Green 1 fluorescent dye present in the RT-PCR assay. The blue LED module was affixed at an angle of ~45° to the plane of the microfluidic chip to minimize excitation light interference on the captured light pathway of the camera unit.

Fluorescence images were captured during the annealing/extension phase (55° C.) of each RT-PCR cycle (Q. Xiang, et al. *Biomedical microdevices,* 2005, 7, 273-279; M. B. Sayers and T. M. Dalton, A real-time continuous flow polymerase chain reactor for DNA expression quantification, Seattle, Wash., 2008; N. Ramalingam, et al. *Biomedical Microdevices,* 2009, 11, 1007-1020) and the mean intensity from each reaction chamber was measured subsequently after RT-PCR completion using IMAGEJ™ image processing and analysis software. A standardized rectangular region (of fixed area) was used to select the fluorescence emission intensities from each reaction chamber, followed by using the measurement analysis tool to obtain the mean fluorescence intensities from the selected region of each chamber.

The fluorescence intensity results were then plotted into real-time PCR amplification curves to allow us to perform gene expression analysis on said GOIs.

To evaluate the specificity of the multiplex RT-PCR process disclosed herein, the amplified PCR products were also visualized and analysed off-chip using conventional gel electrophoresis with a 3.0% agarose gel (Tris-acetate-EDTA or TAE) prestained with ethidium bromide (BIORAD®, Singapore). The gels were typically run for 45 minutes at a constant voltage of 100V in 1× TAE buffer.

Example 1. Microfluidic Sample Preparation and mRNA Extraction

The DYNABEADS® microbeads used in the microfluidic mRNA extraction protocols were coated with oligo $(dT)_{25}$ residues to allow for base binding with the polyA tails at the 3' end of most mRNA polynucleotides, hence resulting in an highly specific isolation protocol. Rather than the capture of total RNA (K. J. Shaw, et al. *Lab Invest*, 2013, 93, 961-966; L. VanHeirstraeten, et al. *LAB ON A CHIP*, 2014, 14, 1519-1526), the specific capture of mRNA molecules would ensure a more relevant nucleic acid sample material for ensuing gene expression analysis.

To validate the feasibility of microfluidic sample preparation and mRNA extraction, the purity of the mRNA extracts obtained from the microfluidic chips as well as from the conventional manual process of using the purification kit was compared. The purity of an RNA sample can be quantified by measuring its absorbance in a spectrophotometer (e.g. NANODROP™ 2000) at different wavelengths of light (i.e. 260 nm and 280 nm) (D. Liu, *Handbook of Nucleic Acid Purification*, CRC Press, 2009). Specifically, the ratio of absorbance of an RNA aliquot at 260 nm and 280 nm is used to assess its purity where an A260/280 ratio of ~2.14 is largely considered to be a pure RNA sample dissolved in Tris-EDTA (TE) buffer at pH 8 (which is the base component of the elution buffer). Lower values are often indicative of the presence of contaminants, such as proteins and phenols, which are strongly absorbent near or at the 280 nm wavelength.

Figure 20:
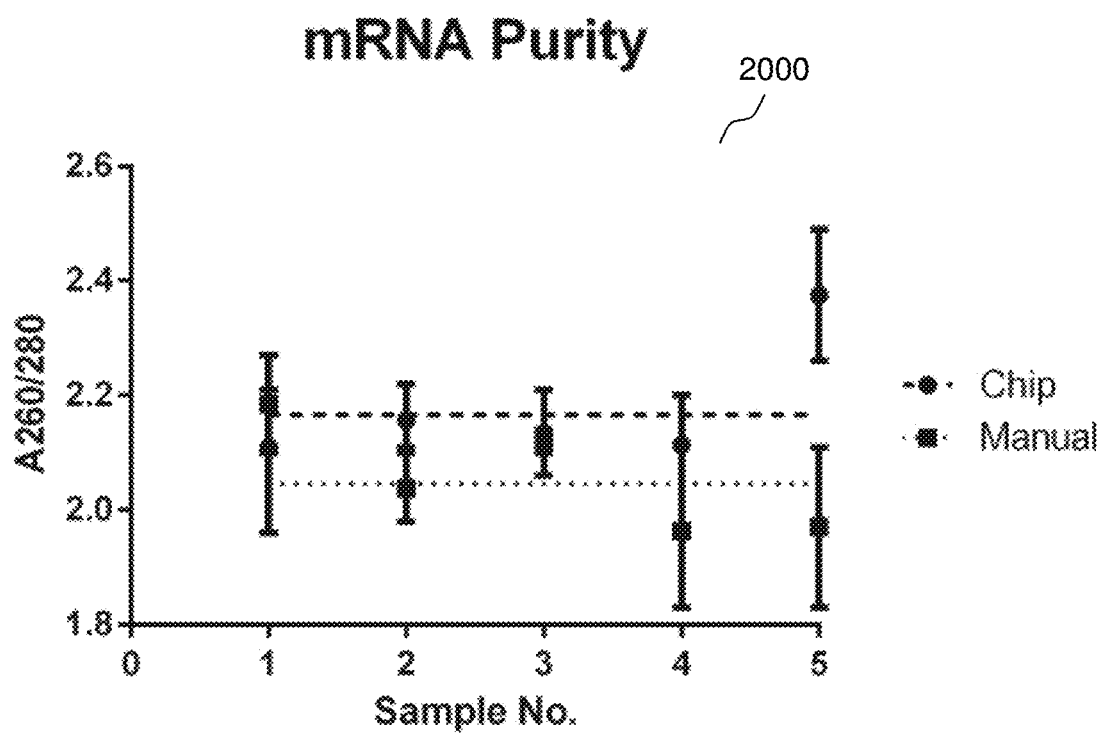
FIG. 20 shows the comparison of A260/280 ratios as a measure of mRNA purity between microfluidic and manual extraction methods from five random mouse tissue samples.

FIG. 20 depicts the comparison 2000 of the purity of mRNA extracts between the microfluidic device disclosed herein and manual extraction method from 5 random mouse tissue samples. It was observed that the best-fit horizontal mean from microfluidic mRNA extraction and from manual extraction mRNA extraction had an A260/280 ratio of ~2.17 and ~2.05 respectively. This indicated that the purity of the microfluidic mRNA extracts was considerably better than the manual mRNA extracts. This noticeable improvement in mRNA purity could be attributed to the sterile enclosed environment provided by on-chip preparation and extraction procedures. The increased quality of the purified mRNA would subsequently ensure more specific and more efficient cDNA amplification in the downstream RT-PCR process. In addition, the microfluidic mRNA extraction protocols also reduced the number of handling steps compared to the manual extraction process, and avoided unnecessary exposure to the external contaminants.

Example 2. Re-Suspension of Dried Preloaded Primers

To perform on-chip RT-PCR, the RT-PCR assay (comprising purified mRNA hybridized to the microbeads and RT-PCR master mix) was loaded into the RT-PCR microfluidic chip and distributed to the 12 reaction chambers to mix with the different sets of dried primers during re-suspension. During the re-suspension process, the chip was left to stand at room temperature for 10 minutes to allow the dried primers to passively fully dissolve in the reagent assay. Active mixing was not performed to avoid any bubble generation which would otherwise result in uneven heat distribution within the reaction assay during thermal cycling.

During the experiments, there were concerns regarding the viability of the primers maintaining their nucleotide structure and functional integrity when exposed to high temperatures during the drying process. If the primer concentrations decreased due to high heat degradation, the efficiency of PCR would drop significantly (M. McPherson and S. Møller, *PCR*, Taylor & Francis, 2007). To verify that the primers maintain their intended functionalities after being subjected to high temperatures, different concentrations of preloaded primers were tested using the ALT target gene and corresponding primers.

Figure 21:
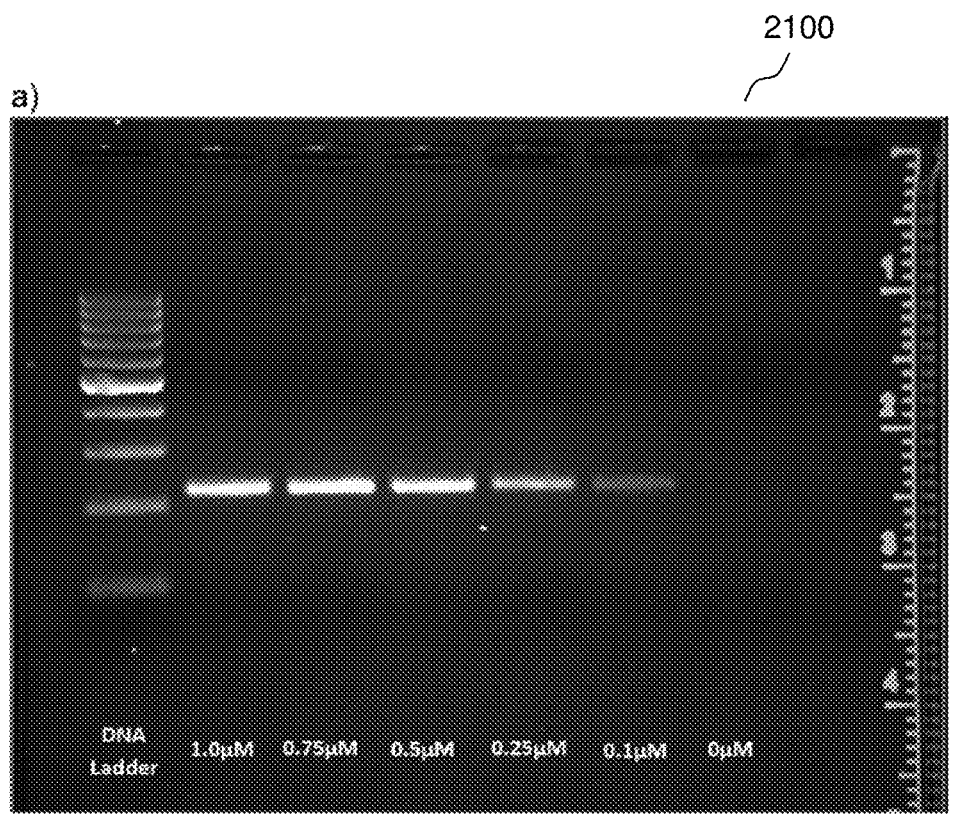
FIG. 21 shows the result of the re-suspension experiment of dried preloaded primers with varying final concentrations in RT-PCR reagent assay for ALT target gene followed by on-chip thermal cycling: a) Gel electrophoresis image showing varying final-primer concentrations (0.1 µM, 0.25 µM, 0.5 µM, 0.75 µM and 1.0 µM) against a 100 bp DNA ladder; b) Signal intensity plot (r.f.u) against final-primer concentration using data derived from gel electrophoresis electropherogram plots. Experiments were performed in triplicates, with error bars shown accordingly.
Figure 21:
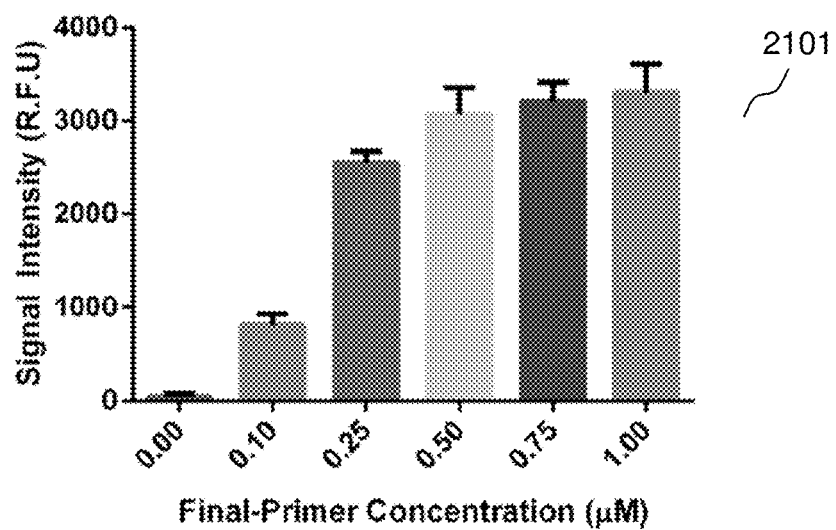

FIG. 21 depicts the differences in PCR amplification efficiencies after on-chip thermal cycling of varying final concentrations of the re-suspended dried primers (FIG. 21a—Gel electrophoresis image 2100 showing varying final-primer concentrations, FIG. 21b—Signal intensity plot 2101 (r.f.u) against final-primer concentration). From FIG. 21, it was observed that high temperature treatment on the primers during the drying process did not have any adverse effect on the functional integrity of the primers. In FIG. 21b, we also observed that the signal intensity of the amplified DNA product after gel electrophoresis saturated at a final-primer concentration of 0.5 μM and higher, indicating that the inventors were able to preload an optimum final-primer concentration of 0.5 μM in the chip without any loss in primers functionality after the drying process.

The process of preloading the primers in dried form was critical towards the design of a microfluidic chip. In the microfluidic chip design disclosed herein, the inventors were able to incorporate a single assay loading inlet to distribute the RT-PCR assays into different reaction chambers preloaded with different primer sets. This surface treatment procedure removed the need to pre-mix different primer sets for multiple RT-PCR assays, thereby significantly simplifying off-chip handling procedures (particularly for multiplex gene expression analysis).

Example 3. Microfluidic Multiplex RT-PCR

Multiple RT-PCR was verified on the PMMA microfluidic chip embodying 12 reaction chambers, preloaded with 0.5 μM final-primer concentrations. Each microfluidic multiplex RT-PCR run embodied a purified mRNA extract from a single liver tissue sample targeting the two GOIs (i.e. AST and ALT) and the housekeeping gene (i.e. β-actin).

Figure 22:
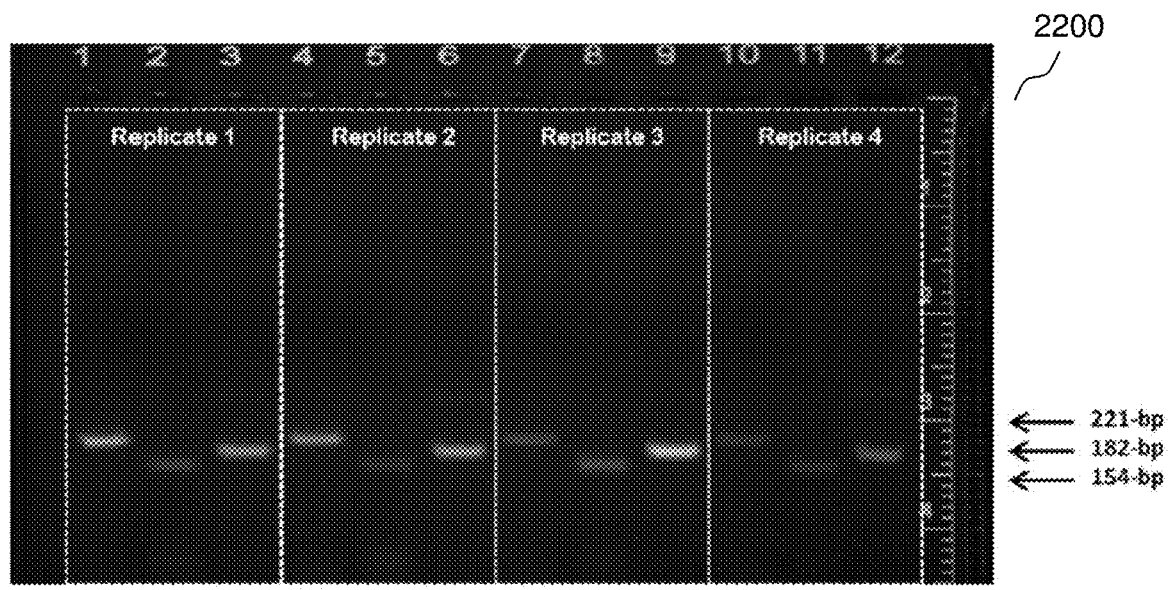
FIG. 22 shows an agarose gel electrophoresis image taken under trans-UV illustrating the specificity of multiplex RT-PCR targeting both ALT and AST genes of interests, and β-actin housekeeping gene from 3×-dosaged mice liver tissue samples. The 12 reaction chambers on the microfluidic chip disclosed herein allowed four replicate groups, each with three target fragments.

To ascertain the specificity of the multiplex RT-PCR reactions, the RT-PCR amplicons were extracted from the chip and analyzed off-chip using conventional gel electrophoresis (see FIG. 22—agarose gel electrophoresis image 2200 taken under trans-UV). Three clear bands were observed on the agarose gel electrophoresis image for each replicate group (for a total of 12) in FIG. 22, wherein the bands at 221-bp, 182-bp and 154-bp belonged to the ALT, AST and β-actin target fragments respectively. This clear band separation with minimal band smearing indicated that our multiplex RT-PCR reaction was highly specific, and verified the usage of mineral oil as a separation medium to eliminate cross-contamination between reaction chambers.

Figure 23:
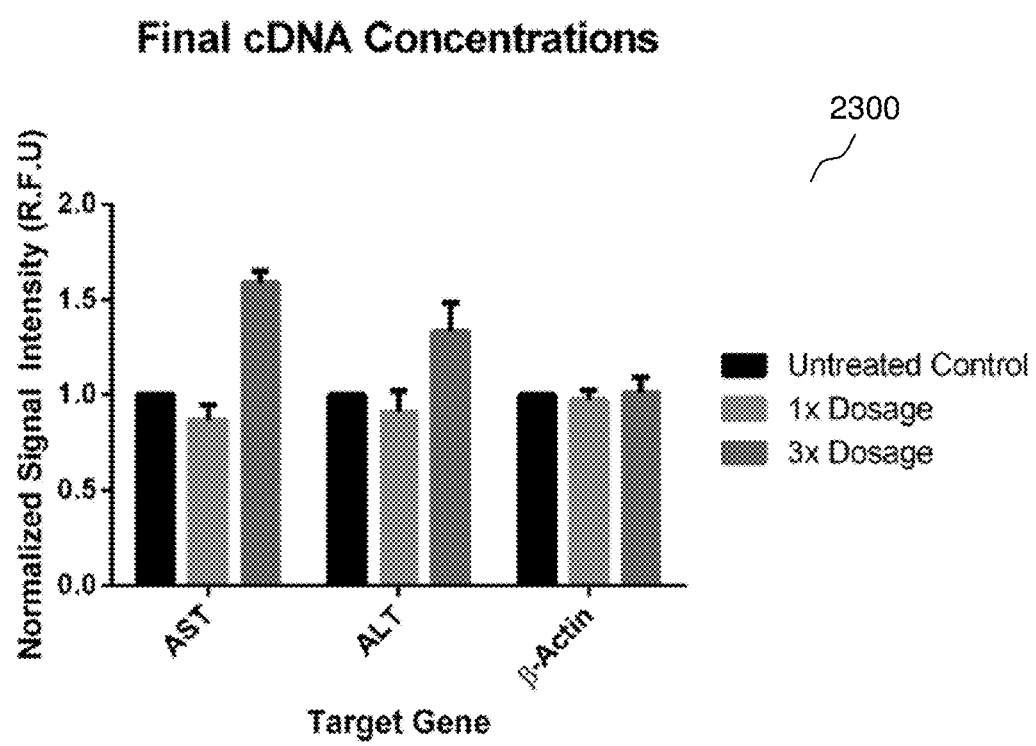
FIG. 23 shows the comparison of the differences in AST, ALT and β-actin cDNA concentrations after varying levels (1× and 3×) of drug treatment (cyclophosphamide, 200 mg/kg body wt.). Experiments were performed in triplicates, with results normalized to the untreated control.

In addition, the average signal intensities obtained from the gel electrophoresis image could be converted into an electropherogram and used for qualitative analysis of end-point RT-PCR (K. J. Shaw, et al. *Lab Invest*, 2013, 93, 961-966; S. J. Baldwin, et al. *Drug metabolism and disposition: the biological fate of chemicals*, 2006, 34, 1063-1069). From the electropherograms, the inventors were able to determine the differences in final cDNA concentrations from liver tissue samples with/without drug treatment, wherein the strength of signal intensities are proportional to the quantity of amplified gene product present (M. McPherson and S. Møller, *PCR*, Taylor & Francis, 2007). This qualitative analytic technique could be used to estimate gene expression levels of the GOIs, and investigate any changes due to cyclophosphamide administration (K. J. Shaw, et al. *Lab Invest*, 2013, 93, 961-966). FIG. 23 shows the comparison 2300 of the differences in AST, ALT and β-actin cDNA concentrations after varying levels (1× and 3×) of drug treatment (cyclophosphamide, 200 mg/kg body wt.). In FIG. 23, the signal intensities for the RT-PCR amplicons from the treated tissue samples (both 1× dosage and 3× dosage) were normalized to those from untreated control tissue sample. This allowed comparing and averaging the data obtained from three biological replicates (i.e. each run encompassing one out of the three drug-treated mice from each treatment group). In view of the statistical significance for the drug-treated groups vis-à-vis the untreated controls, the inventors performed a 2 way ANOVA statistical analysis. This statistical analysis comprised the data obtained from three biological replicates and three technical replicates (from each treatment group), and depicted that the variations of the two GOIs were statistically difference (i.e. p-value<0.0001) between the drug-treated groups and untreated controls.

From FIG. 23, it was observed that the differences in final cDNA concentrations at 1× drug dosage largely had no significant difference when compared to the untreated control samples. It was speculated that this lack of increase in gene expressions levels at 1× drug dosage could be attributed to low (or delayed) drug metabolism of the administered drug in the mice (S. C. Chow and J. Liu, *Design and Analysis of Animal Studies in Pharmaceutical Development*, Taylor & Francis, 1998).

There were, however, significant increases in final cDNA concentrations for both AST and ALT at 3× drug dosage of cyclophosphamide (200 mg/kg body wt.), with 58.7% and 33.3% increases for AST and ALT respectively. These results support the inventors' hypothesis of using a biomolecular diagnostic approach (or NAT) as a viable alternative to conventional Liver Function Tests. These elevations in gene expression levels were generally consistent with data from genetic testing using laboratory mice, wherein significant elevations (in particular ALT) were observed after excessive alcohol consumption (L. Sosa, et al. *International immunopharmacology*, 2005, 5, 301-314) or in mouse fatty liver tissues (S. B. Jadhao, et al. *Hepatolog* (Baltimore, Md.), 2004, 39, 1297-1302), and could be used as evidence of hepatocellular damage. Additionally, it was observed that β-actin mRNA expression levels remained relatively unchanged after a 1× and 3× drug dosage. These results illustrated the constitutive expression behavior of β-actin and helped to validate it as an appropriate choice of housekeeping gene and positive control for our qPCR experiments.

In a separate microfluidic experiment where DNA amplification was performed without the reverse transcription step, genomic contamination was observed to be kept to a minimum. Gel electrophoresis results showed no signal bands for both GOIs as well as the housekeeping gene, indicating the absence of an amplified PCR product. From this result, the inventors were able to unambiguously demonstrate the validity of our intron-spanning primers used for AST, ALT and β-actin mRNA targets.

In short, the increase in genes expression levels for the two GOIs at 3× drug dosage validated the potential for using mRNA target genes based on Liver Function Tests protein biomarkers, and demonstrated the viability of a POCT NAT device for hepatotoxicity assessment.

Example 4. Fluorescent Detection and Gene Expression Analysis

To evaluate the viability of the image capturing system disclosed herein in determining the differences in fluorescence emissions between RT-PCR assays targeting different GOIs, the inventors performed real-time fluorescence emission image captures embodying the 12 reaction chambers. Fluorescence images were captured at each PCR cycle during the annealing/extension phase (55° C.) (Q. Xiang, et al. *Biomedical microdevices*, 2005, 7, 273-279; M. B. Sayers and T. M. Dalton, A real-time continuous flow polymerase chain reactor for DNA expression quantification, Seattle, Wash., 2008) for a total of 35 cycles.

Figure 24:
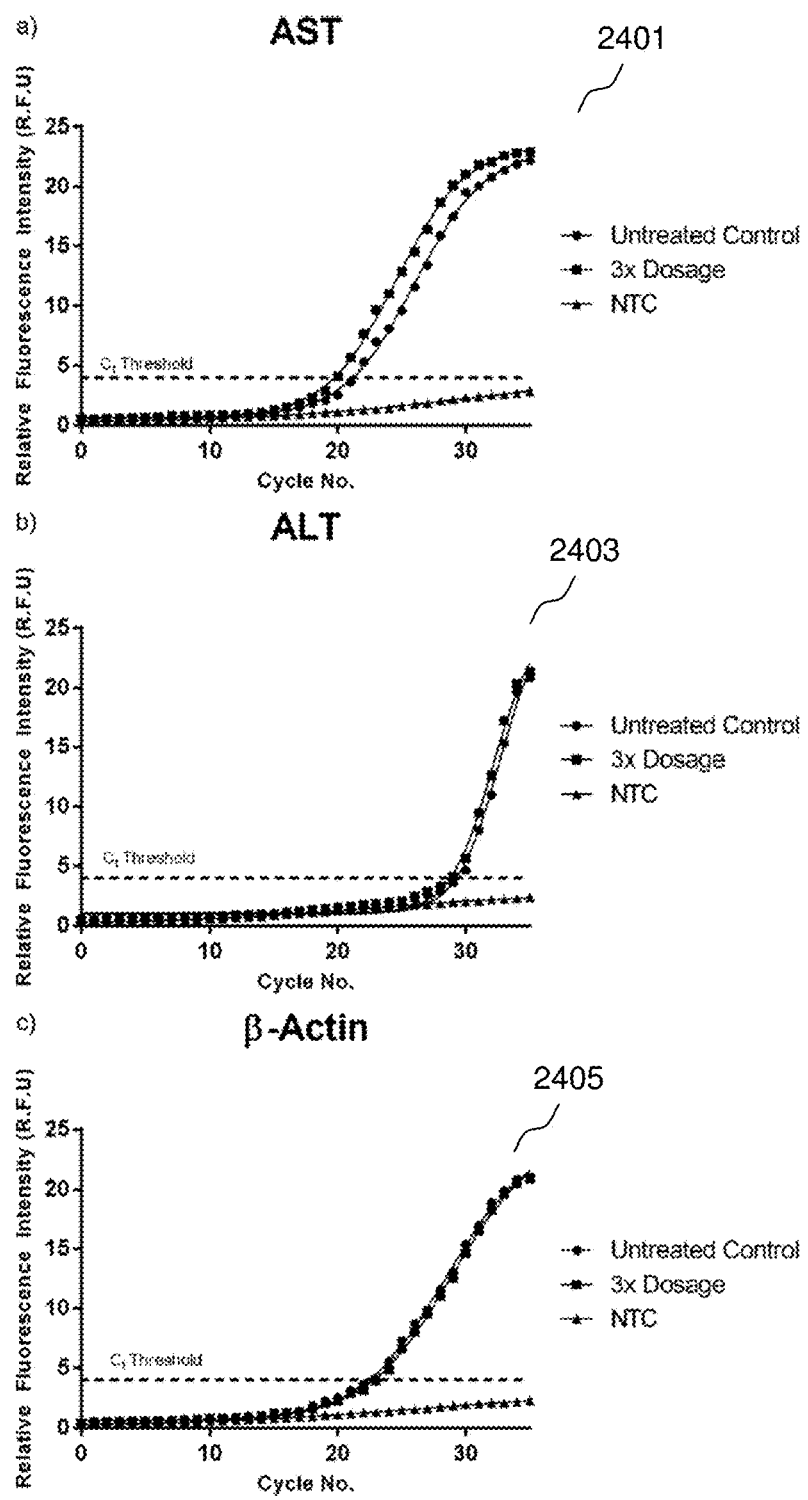
FIG. 24 shows the quantification of real-time fluorescence emission for a) AST, b) ALT and c) β-actin at 3× drug dosage using IMAGEJ™, with images captured at the annealing/extension phase of each PCR cycle.

The intensities in fluorescence emissions derived from captured images were plotted in FIG. 24 to obtain a real-time fluorescence emission curve for both GOIs (i.e. AST and ALT) and the housekeeping gene (i.e. β-actin). FIG. 24 shows the quantification 2401, 2403, 2405 of real-time fluorescence emission for a) AST, b) ALT and c) β-actin at 3× drug dosage using IMAGEJ™, with images captured at the annealing/extension phase of each PCR cycle. With three biological replicates in each treatment group, the inventors were able to account for variation between samples for more precise gene expression measurements (E. Wit and J. McClure, *Statistics for Microarrays: Design, Analysis and Inference*, Wiley, 2004). From the real-time fluorescence amplification plots in FIG. 24, the inventors were able to estimate the initial mRNA concentrations of the samples used via their respective average $C_t$ values; $C_t$ (or cycle threshold) values are often used in quantitative PCR as an indicator of starting/initial concentration of the nucleic acid template (Q. Xiang, et al. *Biomedical microdevices*, 2005, 7, 273-279; E. A. Oblath, et al. *Lab Chip*, 2013, 13, 1325-1332; N. Ramalingam, et al. *Sensors and Actuators, B: Chemical*, 2010, 145, 543-552).

To determine the number of cycles required for the fluorescence signal to exceed that of the background level (N. Ramalingam, et al. *Sensors and Actuators, B: Chemical*, 2010, 145, 543-552), the user-defined $C_t$ threshold value in FIG. 24 was selected based on No Template Control (NTC) fluorescence intensities. The $C_t$ threshold was defined by post-experimental results analysis wherein the number of cycles required for the fluorescence intensities to cross a pre-determined fluorescence threshold (i.e. 20% higher than those of the NTCs) were consistent with the results obtained from a conventional real-time thermal cycler. The $C_t$ values of all six samples (AST-control, AST-3× dosage, ALT-control, ALT-3× dosage, β-actin-control, and β-actin-3× dosage) were correspondingly interpolated and tabulated in Table 2, and compared to determine the relative changes in the mRNA initial concentrations. Table 2 shows that the average $C_t$ value of AST on the microfluidic chip disclosed herein decreased from 20.5 to 19.9 after a 3× drug dosage, while the average $C_t$ value of ALT decreased from 28.8 to 28.5. Conversely, the average $C_t$ value of β-actin remained relatively constant—once again illustrating the constitutive expression behavior of the housekeeping gene.

TABLE 2

Comparison of mean $C_t$ (and corresponding S.D.) values of conventional qPCR machine (CFX96 Touch ™) with the microfluidic setup disclosed herein.

| No. | mRNA Target | CFX96 Touch ™ | Microfluidic Chip |
|---|---|---|---|
| 1 | AST - Control | 20.07 ± 0.02 | 20.5 ± 0.2 |
| 2 | AST - 3x Dosage | 19.34 ± 0.05 | 19.9 ± 0.2 |
| 3 | ALT - Control | 27.28 ± 0.10 | 28.8 ± 0.2 |
| 4 | ALT - 3x Dosage | 26.75 ± 0.07 | 28.5 ± 0.3 |
| 5 | β-Actin - Control | 22.93 ± 0.11 | 23.0 ± 0.2 |
| 6 | β-Actin - 3x Dosage | 23.02 ± 0.08 | 23.1 ± 0.2 |

The presence of the housekeeping gene, β-actin, allowed the inventors to normalize the qPCR experimental data, to minimize possible variations from the experimental setup such as sample preparation and handling, reverse transcription efficiency between sample-sample/run-run repetitions, and DNA amplification efficiencies (M. T. Dorak, *Real-time PCR*, Taylor & Francis, 2007; Life Technologies Corporation, Real-time PCR: Understanding Ct). To obtain a normalized target gene expression level, we used the Livak method to first determine the difference in $C_t$ values between a target gene and the housekeeping gene for a particular sample, before obtaining the $\Delta\Delta C_t$ values (indicative of normalized fold change) (M. T. Dorak, *Real-time PCR*, Taylor & Francis, 2007). From the microfluidic experimental data, it was demonstrated that the normalized fold changes (or up-regulation) for AST and ALT were 1.62 and 1.31 respectively. These values largely indicated that the 3× drug dosaged samples had a higher concentration of initial nucleic acid (or target mRNA in this case) concentration when compared to an untreated control. In the perspective of the differences of up-regulations between AST and ALT, it was observed that ALT had a relatively lower increase in gene expression levels compared to AST. The inventors speculate that this might be due to the reduced (or delayed) response of ALT to cyclophosphamide administration (vis-à-vis AST). Nonetheless, the statistical analysis indicated that AST and ALT collectively illustrated significant differences between the 3× drug dosaged samples and untreated controls.

These results were consistent with the estimates of gene expression changes (i.e. 58.7% and 33.3% increases for AST and ALT respectively) from the inventors' previous qualitative analytic approach (derived from final cDNA concentrations). This consistency of up-regulated gene expression changes from both the qualitative analytic approach and fully-quantitative fluorescent detection methodology herein demonstrated the efficacy of the latter, and its integration with the microfluidic RT-PCR system. More importantly, the inventors validated the AST and ALT GOIs derived from protein biomarkers used in Liver Function Tests, which were illustrated to have been up-regulated after 3× cyclophosphamide treatment.

Collectively, the inventors have designed and demonstrated an integrated LOC system embodying tissue sample preparation, multiplex RT-PCR and real-time fluorescent detection for POCT hepatotoxicity assessment—hence the viability of POCT for hepatotoxicity assessment.

In summary, exemplified herein is a practical POCT hepatotoxicity assessment device, featuring semi-automation, relatively easy-to-use, and "sample-in-answer-out" capabilities for multiplex gene expression analysis. The LOC system disclosed herein embodied the integration of sample preparation, multiplex RT-PCR, and real-time fluorescent detection methodology, and its efficacy was validated by multiplex gene expression analysis on two GOIs (i.e. AST and ALT) derived from Liver Function Tests' biomarkers.

The results from the microfluidic sample preparation module integrated with the multiplex RT-PCR chip has yielded improved purity of mRNA extracts over manual extraction means while significantly reducing off-chip handling procedures for multiple gene targets. The GOIs derived from Liver Function Tests' protein biomarkers validated by the microfluidic RT-PCR results have illustrated up-regulations in their gene expression levels (i.e. increased in final cDNA concentration by 58.7% and 33.3% for AST and ALT respectively) in mice liver tissue samples with a 3× dosage cyclophosphamide drug treatment. Further, the fully-quantitative real-time fluorescent detection methodology has also demonstrated normalized fold changes of 1.62 and 1.31 for AST and ALT respectively, and these results were consistent with the results obtained from using bulky, conventional methodology.

The invention claimed is:

1. A testing device comprising:
a biopsy needle comprising a cutting cannula and an inner stylet which is movable along the cutting cannula; and
a microfluidic chip having
a plurality of chambers connected in a network,
a sample receiving port connected to the network, and
a guide structure in the form of a wall structure protruding from a surface of the microfluidic chip at an edge of the sample receiving port,
wherein a portion of the cutting cannula is received on the guide structure such that a longitudinal axis of the biopsy needle is substantially parallel to the surface of the microfluidic chip,
wherein the inner stylet comprises a notch,
wherein an opening at the portion of the cutting cannula is directed towards the sample receiving port, and
wherein the inner stylet is movable relative to the cutting cannula to position the notch to capture a sample in a distal position from the guide structure and the inner stylet is further movable relative to the cutting cannula to position the notch to transfer, through the opening of the cutting cannula, the captured sample to the sample receiving port in a proximal position to the guide structure, whereby the guide structure directs the captured sample from the opening of the cutting cannula towards the sample receiving port.

2. The testing device as claimed in claim 1, wherein at least one of the plurality of chambers comprises a plurality of magnetic microbeads.

3. The testing device as claimed in claim 1, wherein at least one of the plurality of chambers comprises a flexible thin-film membrane.

4. The testing device as claimed in claim 1, wherein the microfluidic chip further comprises a vent outlet connected to the network.

5. The testing device as claimed in claim 1, wherein the microfluidic chip further comprises:

a vibration actuation mechanism comprising a silica-sand coated piezoelectric disk and a flexible and deformable thin film silica membrane at the sample receiving port, wherein the vibration actuation mechanism is configured to perform vibration shearing to cause lysis of the captured sample received in the sample receiving port;
filtration micro-pillars connecting the sample receiving port to the network; and
an airflow inlet connected to the sample receiving port, wherein an air pump connected to the airflow inlet is capable of generating a flow of air to move the lysed captured sample through the filtration micro-pillars.

6. The testing device as claimed in claim 1, further comprising a frame structure configured to receive the microfluidic chip, wherein the frame structure comprises at least one of an actuator, an electromagnet, a microheater, or a valve controller.

7. The testing device as claimed in claim 6, further comprising a processor connected to the frame structure, the processor configured to control the at least one of an actuator, an electromagnet, a microheater, or a valve controller.

8. The testing device as claimed in claim 6, further comprising:
a light source to serve as excitation source for fluorescent dye in at least one of the plurality of chambers of the microfluidic chip; and
a camera to capture images of excitation of the fluorescent dye for fluorescence detection.

9. The testing device as claimed in 6, further comprising:
a main body encasing the frame structure and the microfluidic chip, wherein the main body is configured to receive the biopsy needle such that the biopsy needle is received by the guide structure of the microfluidic chip on the frame structure of the testing device; and
a handgrip attached to the main body.

* * * * *

SEQUENCE LISTING

<160> NUMBER OF SEQ ID NOS: 9

<210> SEQ ID NO 1
<211> LENGTH: 182
<212> TYPE: DNA
<213> ORGANISM: Mus musculus

<400> SEQUENCE: 1

```
gctgacttct tagggcgatg gtacaatggt acagataaca agaacacacc aatctacgta    60
tcatcaccaa cctgggagaa ccataatgct gtgttttctg ccgccggttt taaggacatt   120
cggccctatt gctactggga tgcggagaag agaggactgg acctccaggg tttcctgaat   180
ga                                                                  182
```

<210> SEQ ID NO 2
<211> LENGTH: 20
<212> TYPE: DNA

```
<213> ORGANISM: Artificial sequence
<220> FEATURE:
<223> OTHER INFORMATION: Synthetic construct

<400> SEQUENCE: 2
gctgacttct tagggcgatg                                                   20

<210> SEQ ID NO 3
<211> LENGTH: 20
<212> TYPE: DNA
<213> ORGANISM: Artificial sequence
<220> FEATURE:
<223> OTHER INFORMATION: Synthetic construct

<400> SEQUENCE: 3
tcattcagga aaccctggag                                                   20

<210> SEQ ID NO 4
<211> LENGTH: 221
<212> TYPE: DNA
<213> ORGANISM: Mus musculus

<400> SEQUENCE: 4
ctgcagaccc gaacaacata tttctgtcca caggggccag cgatgccatc gtgaccatgc       60
tcaagctgct ggtagccggc gagggccgtg cgcgaaccgg tgtactcatt cccattcctc      120
agtacccact gtactcagct gcgctggctg agctggacgc cgtgcaagtg gactactacc      180
tgaacgaaga gcgcgcctgg gctcttgaca tcgctgagct g                          221

<210> SEQ ID NO 5
<211> LENGTH: 20
<212> TYPE: DNA
<213> ORGANISM: Artificial sequence
<220> FEATURE:
<223> OTHER INFORMATION: Synthetic construct

<400> SEQUENCE: 5
ctgcagaccc gaacaacata                                                   20

<210> SEQ ID NO 6
<211> LENGTH: 20
<212> TYPE: DNA
<213> ORGANISM: Artificial sequence
<220> FEATURE:
<223> OTHER INFORMATION: Synthetic construct

<400> SEQUENCE: 6
cagctcagcg atgtcaagag                                                   20

<210> SEQ ID NO 7
<211> LENGTH: 154
<212> TYPE: DNA
<213> ORGANISM: Mus musculus

<400> SEQUENCE: 7
ggctgtattc ccctccatcg tgggccgccc taggcaccag ggtgtgatgg tgggaatggg       60
tcagaaggac tcctatgtgg gtgacgaggc ccagagcaag agaggtatcc tgaccctgaa      120
gtaccccatt gaacatggca ttgttaccaa ctgg                                  154

<210> SEQ ID NO 8
<211> LENGTH: 20
<212> TYPE: DNA
<213> ORGANISM: Artificial sequence
```

```
-continued

<220> FEATURE:
<223> OTHER INFORMATION: Synthetic construct

<400> SEQUENCE: 8
ggctgtattc ccctccatcg                                              20

<210> SEQ ID NO 9
<211> LENGTH: 22
<212> TYPE: DNA
<213> ORGANISM: Artificial sequence
<220> FEATURE:
<223> OTHER INFORMATION: Synthetic construct

<400> SEQUENCE: 9
ccagttggta acaatgccat gt                                           22
```